(12) United States Patent
Lombardo et al.

(10) Patent No.: US 11,517,302 B2
(45) Date of Patent: Dec. 6, 2022

(54) KNOTLESS INSTABILITY ANCHOR

(71) Applicant: Conmed Corporation, Utica, NY (US)

(72) Inventors: Giuseppe Lombardo, New Port Richey, FL (US); Grady Breslich, Bradenton, FL (US); Peter Miller, Largo, FL (US); Adrian Bosworth, Bradenton, FL (US)

(73) Assignee: Conmed Corporation, Utica, NY (US)

( * ) Notice: Subject to any disclaimer, the term of this patent is extended or adjusted under 35 U.S.C. 154(b) by 266 days.

(21) Appl. No.: 16/764,487

(22) PCT Filed: Nov. 15, 2018

(86) PCT No.: PCT/US2018/061168
§ 371 (c)(1),
(2) Date: May 15, 2020

(87) PCT Pub. No.: WO2019/099599
PCT Pub. Date: May 23, 2019

(65) Prior Publication Data
US 2020/0360009 A1    Nov. 19, 2020

Related U.S. Application Data

(60) Provisional application No. 62/586,383, filed on Nov. 15, 2017.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0406* (2013.01);
(Continued)

(58) Field of Classification Search
CPC .......... A61F 2/0811; A61F 2002/0888; A61B 17/0401; A61B 2017/0406; A61B 2017/0464; A61B 2017/0409; A61B 17/06166; A61B 2017/0459; A61B 17/0469; A61B 2017/06185; A61B 2017/0414
See application file for complete search history.

(56) References Cited

U.S. PATENT DOCUMENTS 6,517,578 B2    2/2003    Hein
8,894,684 B2    11/2014   Sengun
(Continued)

OTHER PUBLICATIONS

International Search Report Form PCT/ISA/220, International Application No. PCT/US2018/061168, pp. 1-12, dated Feb. 27, 2019.

*Primary Examiner* — Katherine M Shi
(74) *Attorney, Agent, or Firm* — Bond, Schoeneck & King, PLLC; Frederick J. M. Price

(57) ABSTRACT

A knotless instability anchor having an anchor having a first side and a second side with a suture material passing therethrough from the first side to the second side. The suture material has an adjustable loop extending from the first side of the anchor and a first limb and a second limb extending from the second side of the anchor. A splice is formed in the first limb between a first end of the first limb and the anchor. A self-collapsing loop is formed in the first limb between the first end and the splice. The second limb extends through the splice in the first limb.

18 Claims, 35 Drawing Sheets

(52) U.S. Cl.
CPC ........ *A61B 2017/0409* (2013.01); *A61B 2017/0464* (2013.01); *A61B 2017/06185* (2013.01)

(56) References Cited

U.S. PATENT DOCUMENTS

| | | |
|---|---|---|
| 9,060,763 B2 | 6/2015 | Sengun |
| 9,192,373 B2 | 11/2015 | Sengun |
| 9,271,716 B2 | 3/2016 | Sengun |
| 9,314,241 B2 | 4/2016 | Stone et al. |
| 9,357,992 B2 | 6/2016 | Stone et al. |
| 9,370,350 B2 | 6/2016 | Norton |
| 9,421,008 B2 | 8/2016 | Burkhart et al. |
| 9,463,911 B2 | 10/2016 | Choi et al. |
| 9,826,971 B2 | 11/2017 | Lombardo et al. |
| 9,962,150 B2 | 5/2018 | Rodriguez et al. |
| 10,064,716 B2 | 9/2018 | Norton |
| 10,245,016 B2 | 4/2019 | Zajac et al. |
| 10,258,320 B2 | 4/2019 | Dreyfuss et al. |
| 10,265,060 B2 | 4/2019 | Dooney, Jr. et al. |
| 10,271,833 B2 | 4/2019 | Sengun |
| 10,368,856 B2 | 8/2019 | Stone et al. |
| 10,405,968 B2 | 9/2019 | Gustafson et al. |
| 10,595,845 B2 | 3/2020 | Burkhart et al. |
| 10,631,848 B2 | 4/2020 | Sengun et al. |
| 2016/0374662 A1 | 12/2016 | Dreyfuss et al. |
| 2017/0119369 A1 | 5/2017 | Lombardo et al. |
| 2017/0128063 A1 | 5/2017 | Jackson | ns
KNOTLESS INSTABILITY ANCHOR

CROSS-REFERENCES TO RELATED APPLICATIONS

This application is a national stage application under 35 U.S.C. 371 based on international patent application PCT/US18/61168 filed on Nov. 15, 2018, which claims priority to U.S. Provisional Patent Application Ser. No. 62/586,383, filed on Nov. 15, 2017.

BACKGROUND OF THE INVENTION

1. Field of the Invention

The present disclosure is directed generally to a suture anchor device for soft tissue to bone repair procedures and, more particularly, to a knotless instability anchor with a sliding construct for tissue tensioning and a splice to secure the tissue in relative position to the bone.

2. Description of Related Art

Suture anchors are commonly used to repair soft tissue to bone in surgical procedures. Typically, they are inserted into a pre-formed hole and then the sutures are passed through the tissue to be repaired. In many cases, a sliding knot it tied thereby allowing for better tissue tensioning control as the surgeon manipulates the sliding knot to bring the tissue into apposition with the bone. In doing so, the tissue is naturally brought back to the point of origin of the suture and comes to rest directly over the pre-formed hole or pilot hole. To secure the sliding knot, the surgeon will tie one or more alternating half-hitch knots to complete the procedure. The act of tying a knot presents a number of challenges to the surgeon especially when doing them arthroscopically. Furthermore, in some cases, knots have been implicated as the source of post-operative pain caused by irritation from the knot stack.

Various types of suture anchors have been deployed which fasten the suture in place without requiring the surgeon to tie a knot. Some designs capture the suture between two anchor components while others utilize an interference fit between the anchor and the bone tunnel. Many designs using these methods of fixation require the driver to be engaged with the anchor while tensioning the suture to bring the tissue into apposition with the bone. Since the driver is still engaged in the pilot hole, it prevents the tissue from being able to be tensioned so that it directly over the pilot hole (suture origin) thus giving a less than ideal tissue position, and encumbering the adjustment of suture tension.

Conventional solutions to the problem of tissue position by the implementation of an adjustable loop which is formed around the tissue to be repaired exist. In this instance, the anchor is installed in bone and the driver is removed. One limb of the suture is free and passed through the tissue then into a loading filament which passes it back through the suture limb, creating a one-way loop. This requires the standing end of the suture to remain fixed so that it acts as a finger trap when the loop is tensioned thereby preventing loop loosening. This method also requires a long length of suture to pass through or around the tissue before the loop is reduced which can cause tissue damage by abrasion. Furthermore, the fixed end must reside deep in the hole and must not migrate or tensioning will be limited. Lastly, this type of device is comprised of a rigid material which can damage tissue if it pulls out of the hole during healing.

Therefore, a need exists for a simple-to-use suture anchor comprised of soft materials which secures suture without the need to tie a knot and which facilitates the ability to adjust, maintain, and position tissue in desired location of the pilot hole during anchor installation.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional knot or knotless suture constructs. For example, knots and knotless constructs can be large and rigid enough to cause irritation, and require constant engagement by the driver during installation which results in less than ideal positioning of the tissue over the bone hole (as described above). Therefore, a need exists for a simple-to-use suture anchor comprised of soft materials which secures suture without the need to tie a knot and which facilitates the ability to adjust, maintain, and position tissue in desired location of the pilot hole during anchor installation. Various embodiments of the present invention may be advantageous in that they may solve or reduce one or more of the potential problems and/or disadvantages discussed herein.

The present disclosure is directed to an inventive configuration, structure, and resulting function of a knotless instability anchor and a method for securing a first body in relative position to a bone hole. The knotless instability anchor includes an anchor having a first side and a second side with a suture material passing therethrough from the first side to the second side. The suture material has an adjustable loop extending from the first side of the anchor and a first limb and a second limb extending from the second side of the anchor. A splice is formed in the first limb between a first end of the first limb and the anchor. A self-collapsing loop is formed in the first limb between the first end and the splice. The second limb extends through the splice in the first limb.

According to an another aspect, a method of securing a first body in relative position to a bone hole includes (but is not limited to) the steps of: (i) providing a knotless instability anchor comprising an anchor having a first side and a second side with a suture material passing therethrough from the first side to the second side, wherein the suture material has an adjustable loop extending from the first side of the anchor and a first limb and a second limb extending from the second side of the anchor, a splice formed in the first limb between a first end of the first limb and the anchor, and a self-collapsing loop formed in the first limb between the first end and the splice; (ii) passing the second limb through the splice in the first limb; (iii) attaching a passing limb to the adjustable loop via a releasable connection; (v) implanting the anchor into a bone hole; (vi) passing the first limb over at least a portion of the first body to an opposing side of the first body; and (vii) pulling the first limb through the adjustable loop on the opposing side of the first body.

Suture material or sutures, as the terms are used and described herein, include monofilament or multi-filament suture as well as any other metallic or non-metallic filamentary or wire-like material suitable for performing the function of a suture. This material can include both bioabsorbable and non-absorbable materials.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

As a brief background, suture anchors, as the term is used herein, can include soft suture anchors. Soft suture anchors are formed from filaments of suture material which are retained within pre-formed bone holes by being deformable to increase their diameter to a size greater than that of the bone hole, to thereby reside within the cancellous bone and under the bone cortex. One such suture anchor is disclosed in U.S. Pat. No. 9,826,971. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652, the contents of which are hereby incorporated by reference herein in their entirety) and a suture or filament portion. Some methods and devices for inserting/deploying such all-suture anchors are known, examples of which are disclosed in U.S. Pat. No. 9,173,652.

Figure 1:
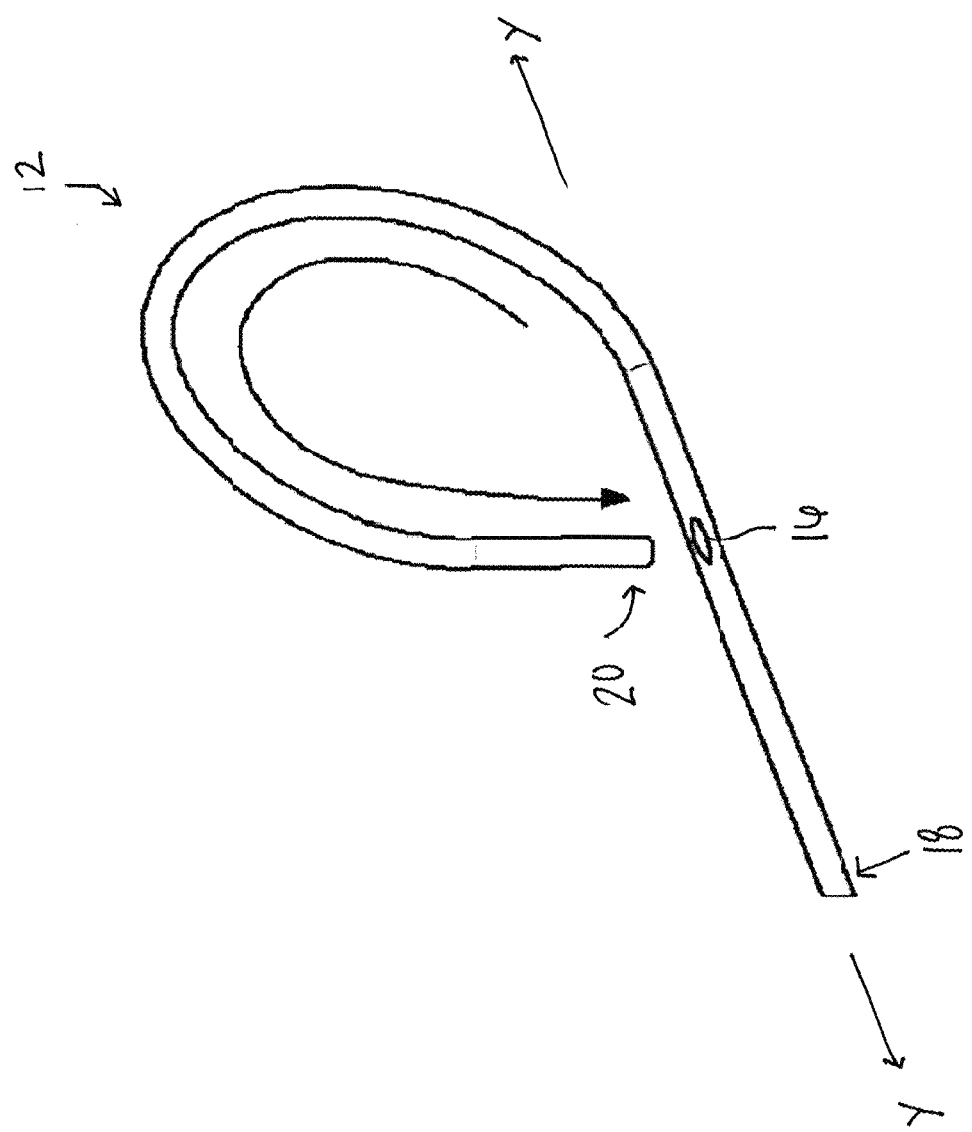
FIG. 1 is a perspective view schematic representation of the suture strand at the first step of creating the pre-deployment configuration of the knotless instability anchor, according to an embodiment.
Figure 2:
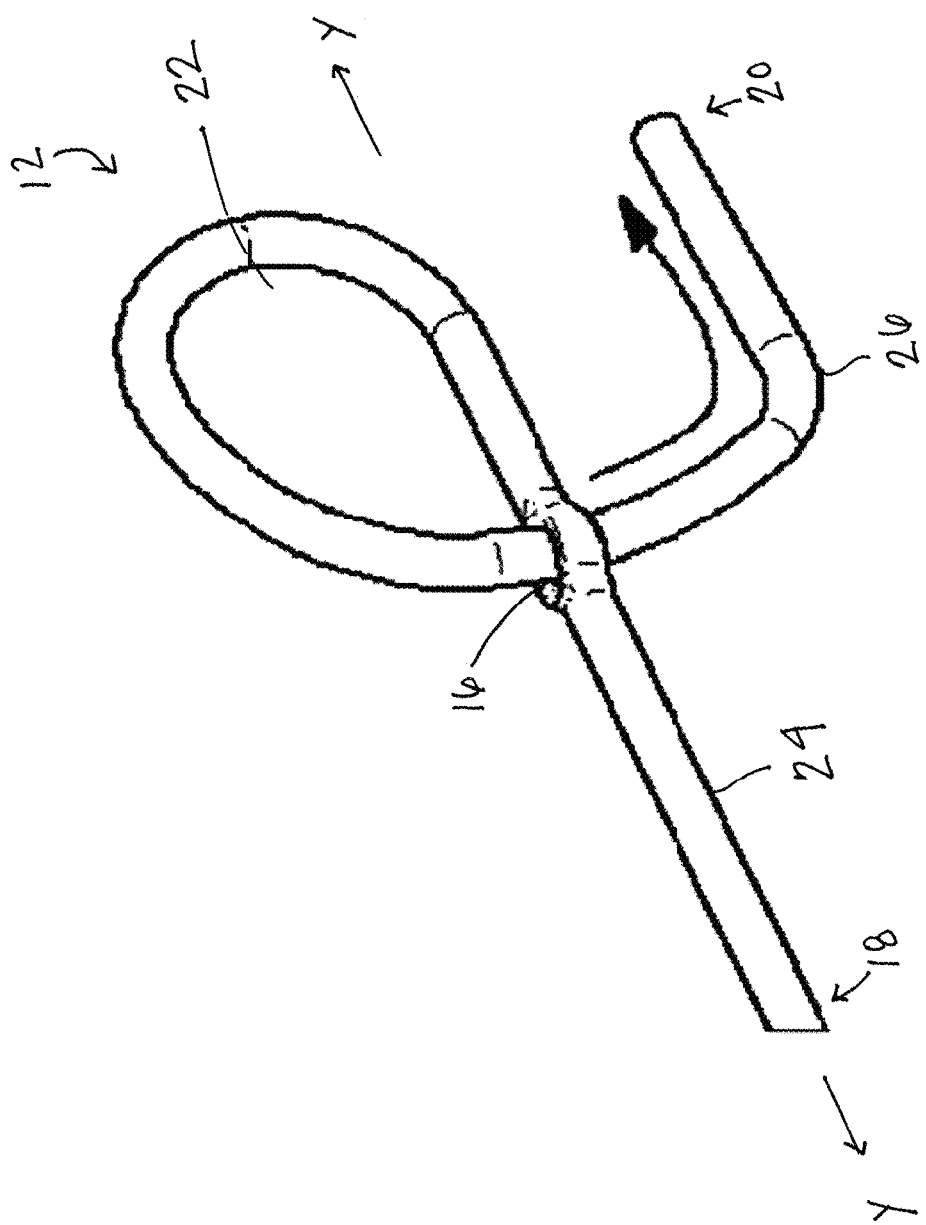
FIG. 2 is a perspective view schematic representation of the suture strand at the second step of creating the pre-deployment configuration of the knotless instability anchor, according to an embodiment.
Figure 4:
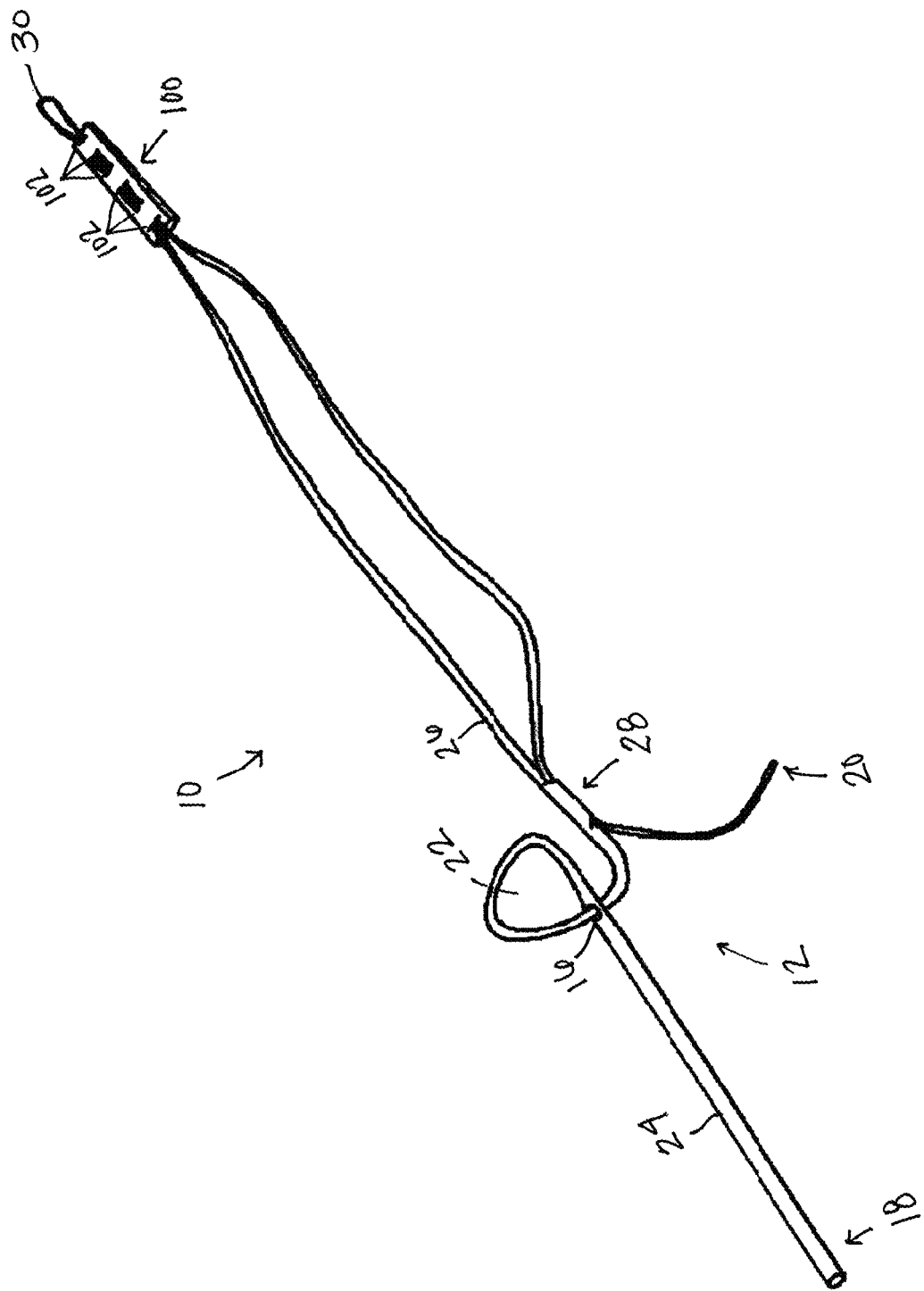
FIG. 4 is a perspective view schematic representation of the suture strand at the fourth step of creating the pre-deployment configuration of the knotless instability anchor, according to an embodiment.
Figure 5:
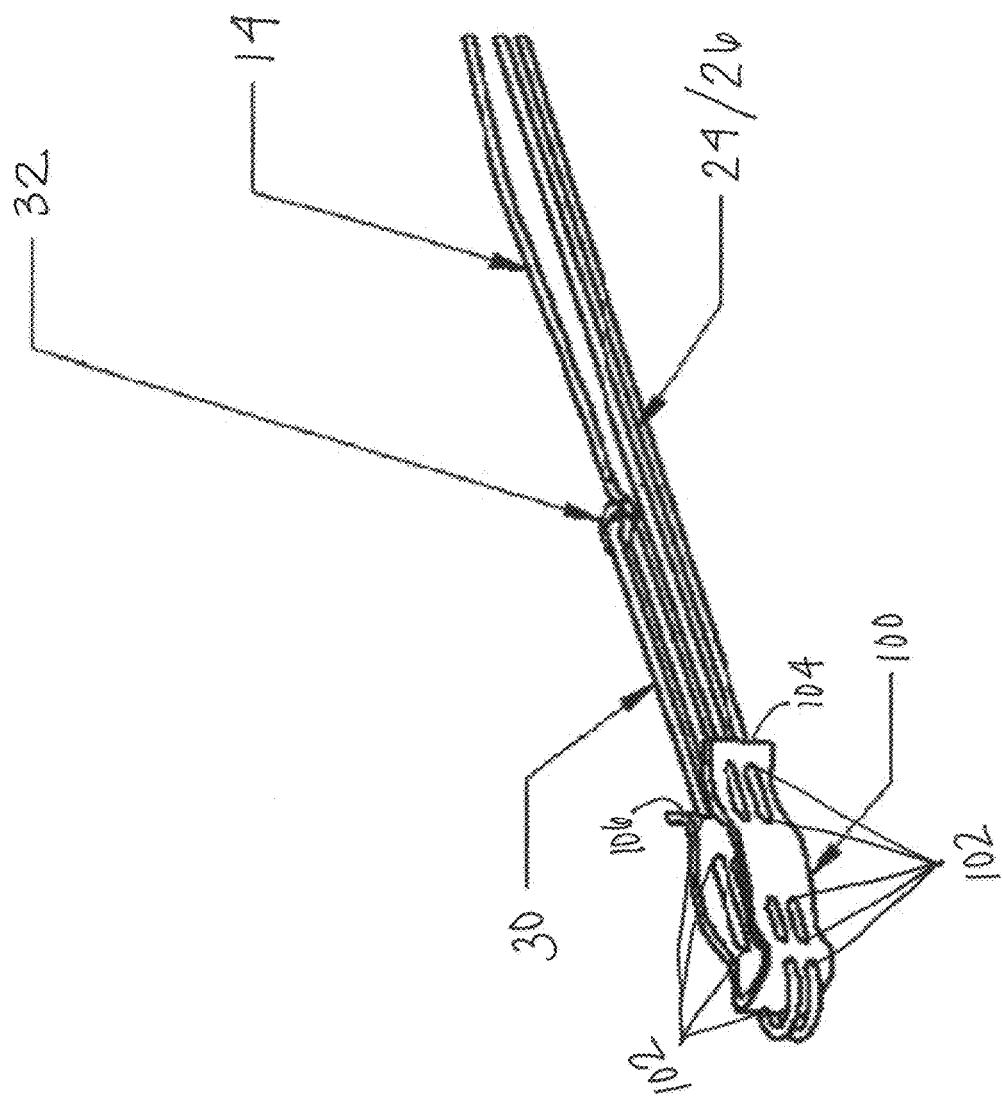
FIG. 5 is a perspective view schematic representation of the suture strand with a passing limb attached, according to an embodiment.
Figure 6:
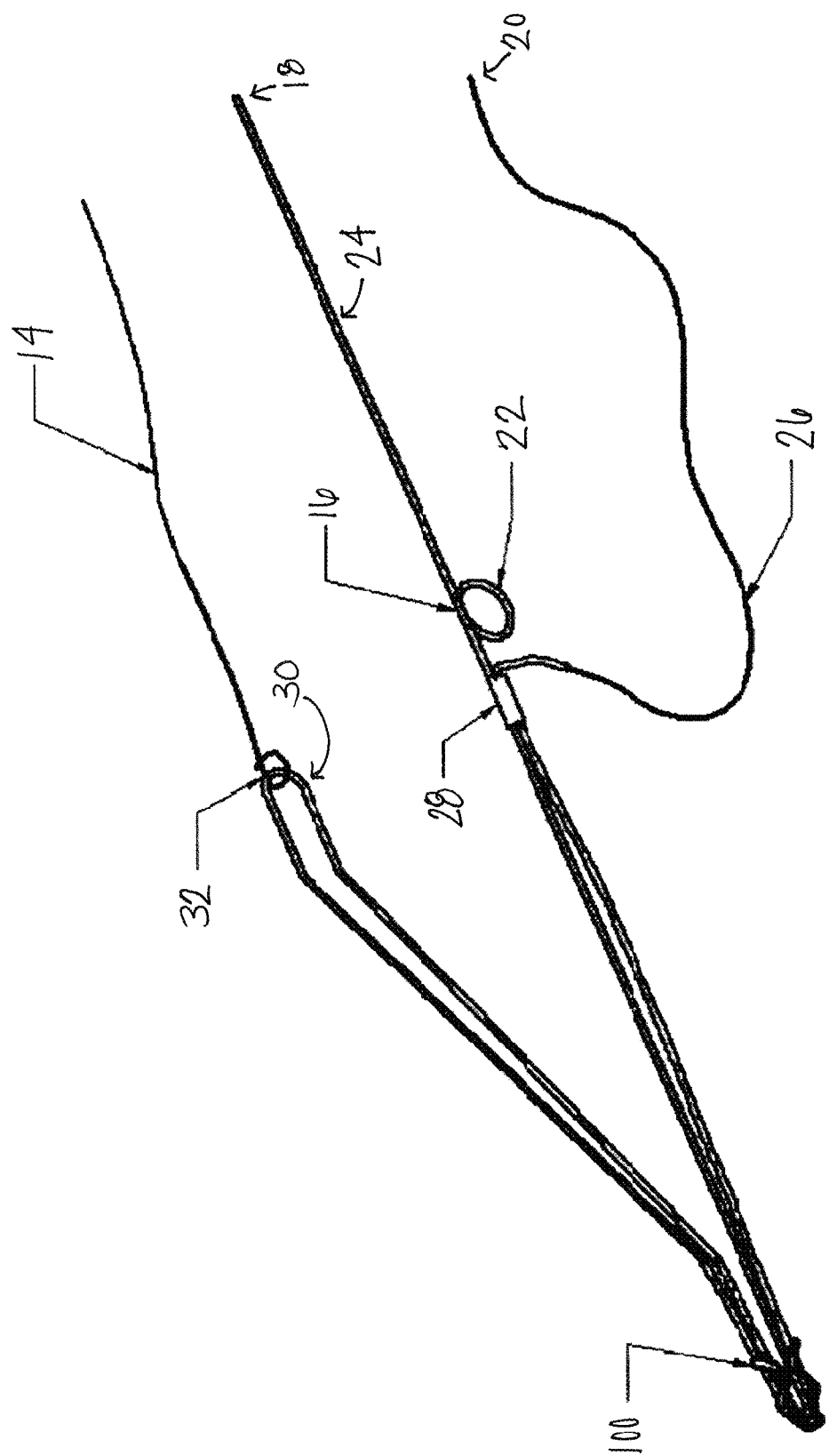
FIG. 6 is a perspective view schematic representation of the suture strand with a passing limb attached, according to an alternative embodiment.

Referring now to the figures, wherein like reference numerals refer to like parts throughout, an embodiment of the present invention includes a knotless instability anchor 10 including a woven material (anchor) 100, a strand of suture (or "suture strand") 12, and a passing filament (or "passing limb") 14 (FIGS. 4-6). FIGS. 1-2 show perspective views schematic representations of the suture strand 12 at the first and second steps of creating the pre-deployment configuration of the knotless instability anchor 10, according to an embodiment. To prepare the suture strand 12 for use, a pierce (or aperture) 16 is formed at or near a first end 18 of the suture strand 12, as shown in FIG. 1. In an embodiment, the pierce 16 is approximately ⅓ of the length of the suture strand 12 from the first end 18. A second end 20 of the suture strand 12 is rotated proximally (or counterclockwise) along a central longitudinal y-y axis through the suture strand 12. The second end 20 is passed through the pierce 16, as shown in FIG. 2, creating a self-collapsing loop 22 with a first limb 24 and a second limb 26 of the suture strand 12 extending therefrom. The second end 20 is pulled through the pierce 16 and away from the first end 18, as also shown in FIG. 2.

Figure 3:
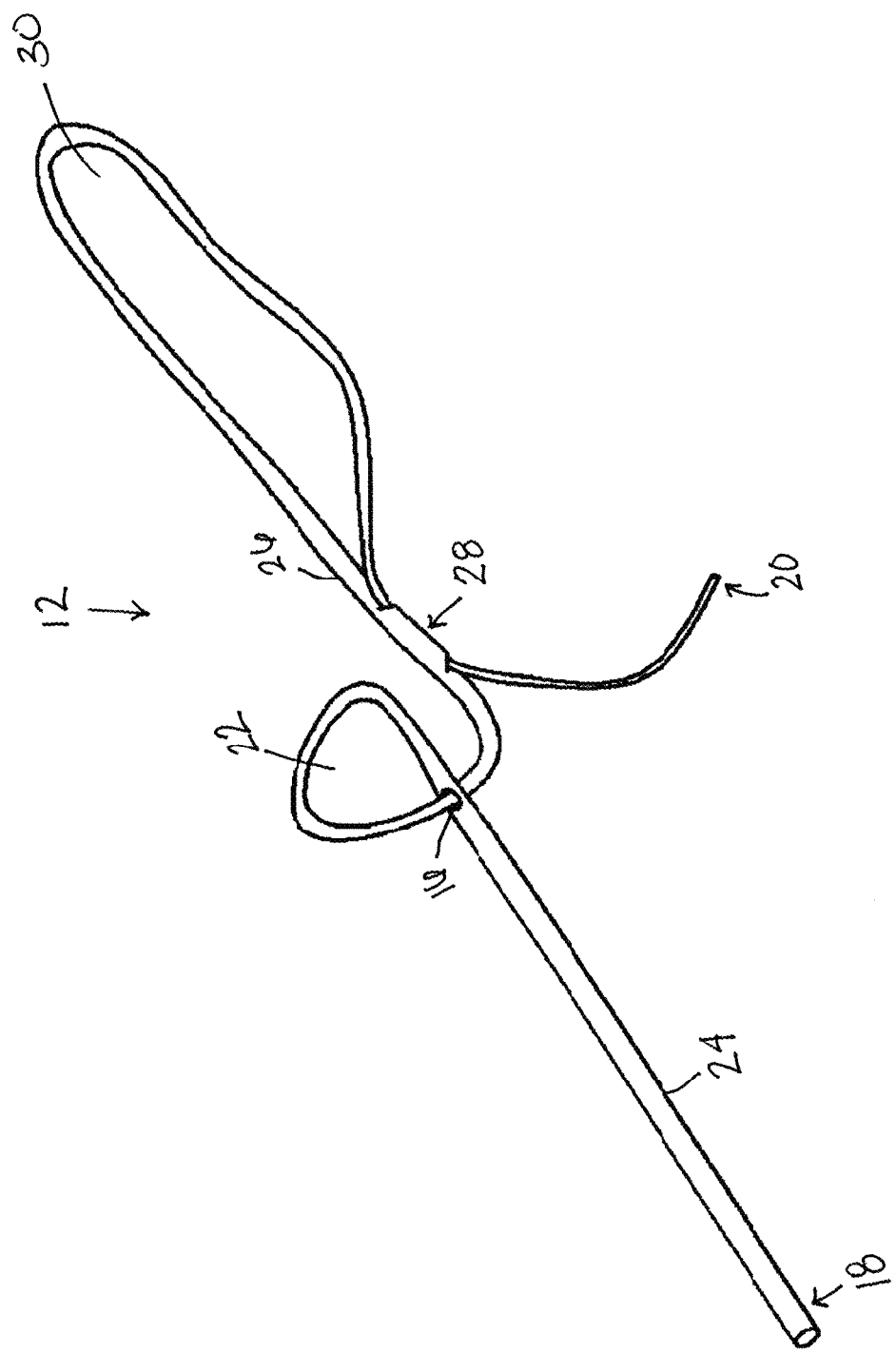
FIG. 3 is a perspective view schematic representation of the suture strand at the third step of creating the pre-deployment configuration of the knotless instability anchor, according to an embodiment.

Turning now to FIG. 3, there is shown a perspective view schematic representation of the suture strand 12 in a third step of creating the pre-deployment configuration of the knotless instability anchor, according to an embodiment. As shown in FIG. 3, a splice 28 is created in the second limb 26 of the suture strand 12. In one embodiment, the splice 28 is an eye splice approximately 3-6 mm in length. In an embodiment, the splice 28 is 2-5 mm proximal from the second end 20 of the suture strand 12. As also shown in FIG. 3, the second end 20 of the suture strand 12 is passed through the splice 28. The second end 20 is pulled through the splice 28, creating an adjustable loop 30 in the second limb 26 of the suture strand 12.

Referring now to FIG. 4, there is shown a perspective view schematic representation of the suture strand 12 in a fourth step of creating the pre-deployment configuration of the knotless instability anchor, according to an embodiment.

At the fourth step, the adjustable loop 30 is pulled through a woven material 100 which functions as an soft all suture anchor (e.g., Y-Knot anchor), as shown in FIG. 4. In the depicted embodiment, the woven material 100 is a flat, soft woven material, such as dyneema. In the depicted embodiment, the woven material 100 has six passing locations 102 wherein the adjustable loop 30 (suture strand 12) either enters or exits the woven material 100. In a preferred embodiment, the woven material 100 has eight passing locations 102 (alternatively, there can be any number of multiple passing locations).

Turning now to FIG. 5, there is shown a perspective view schematic representation of the suture strand 12 with a passing limb 14 attached, according to an embodiment. As shown in FIG. 5, the adjustable loop 30 has been pulled through the woven material 100 such that the suture strand 12 extends from either side 104, 106 of the woven material 100. In the depicted embodiment, the woven material 100 can be a flat suture tape. FIG. 5 also shows the passing limb 14 releasably connected to the adjustable loop 30 via a releasable connection 32. A releasable connection 32 can be any known type of connection that can easily be undone, such as a slip knot, for example. Referring now briefly to FIG. 6, there is shown a perspective view schematic representation of a suture strand 12 with the releasable passing limb 14 attached, according to an alternative embodiment. In the depicted embodiment, the woven material 100 can be a Y-Knot anchor (as further described with respect to FIGS. 15 and 16).

Figure 7:
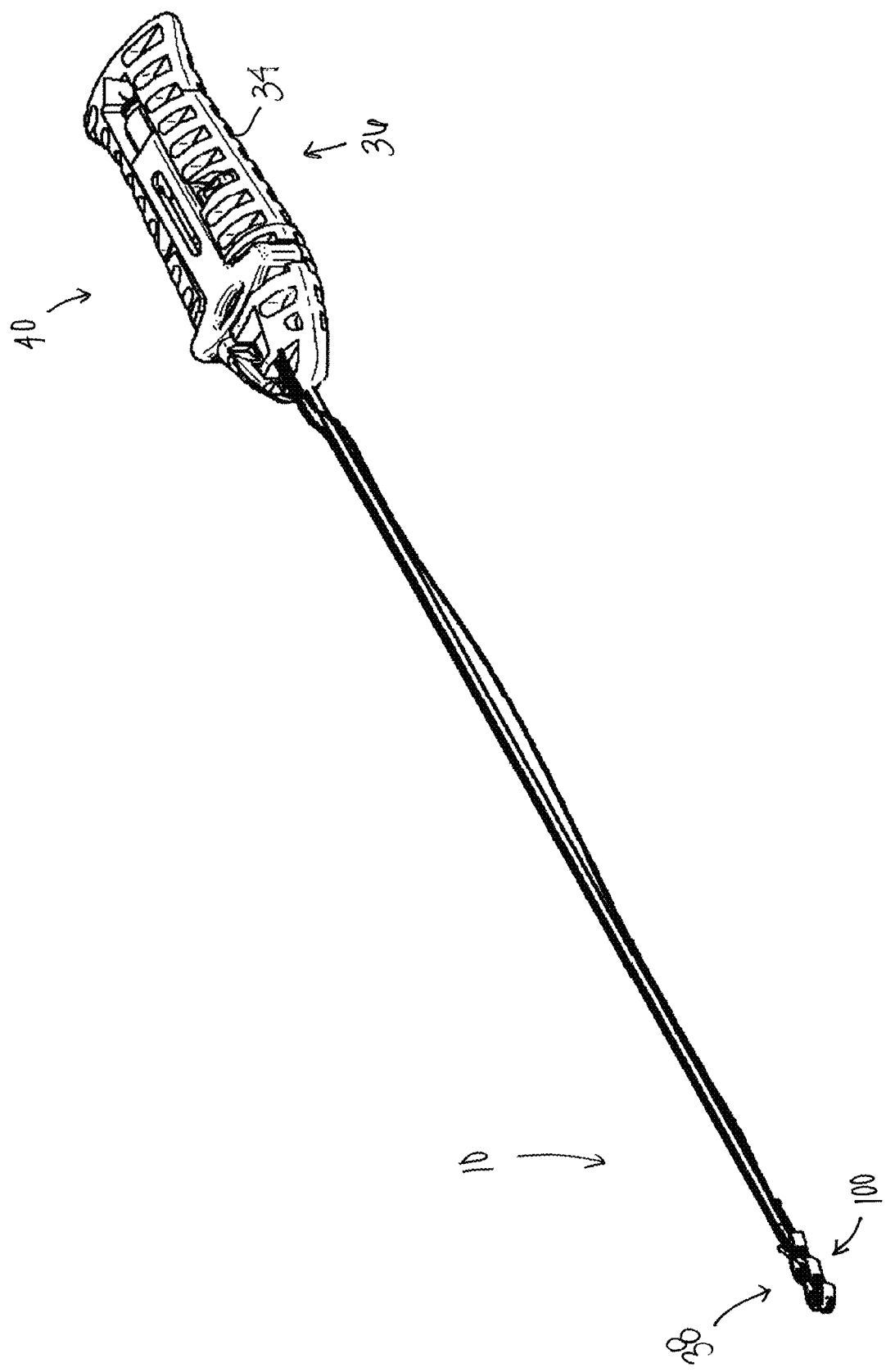
FIG. 7 is a perspective view schematic representation of a driver loaded with the knotless instability anchor in the pre-deployment configuration, according to an embodiment.

Referring now to FIG. 7, there is shown a perspective view schematic representation of a driver 40 loaded with the knotless instability anchor 10 in the pre-deployment configuration, according to an embodiment. The driver 40 can be composed of any suitable material, such as stainless steel. The driver 40 may comprise a handle 34 at a proximal end 36 and a forked distal end 38. To use the knotless instability anchor 10, the driver 40 is loaded with the knotless instability anchor 10 in the pre-deployment configuration. Prior to deploying the knotless instability anchor 10, the surgical area is prepared. Generally, an incision is made through the skin distal the bone with the injury to be repaired. Next, a cannula is inserted through the incision and into the area (e.g., joint space) surrounding the bone. Thereafter, a drill guide is inserted through the cannula and placed in position against the bone. A drill bit is inserted through the drill guide to create a bone hole. Next, the drill bit is removed and the driver 40 loaded with the knotless instability anchor 10 is inserted into the bone hole. Thereafter, the driver 40 pushes the woven material 100 of the knotless instability anchor 10 into the bone hole, as shown in FIG. 34.

Figure 8:
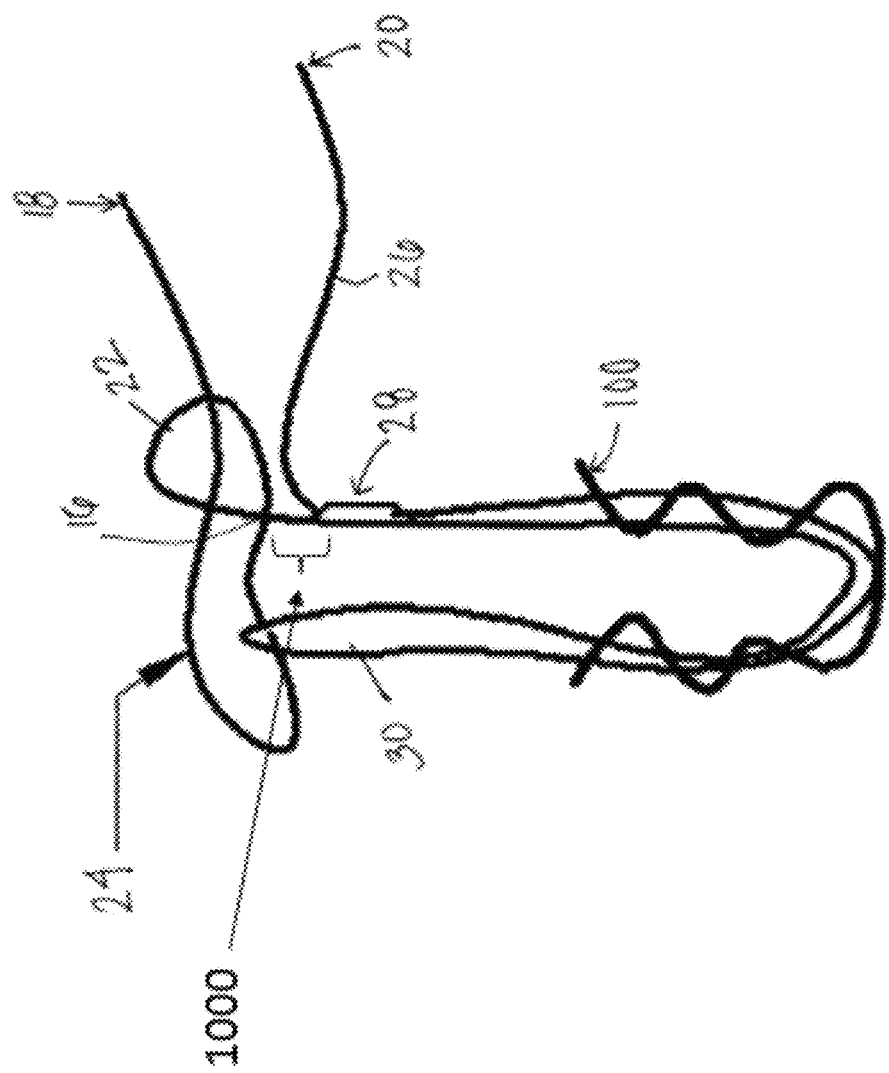
FIG. 8 is a side view schematic representation of the knotless instability anchor in the post-deployment configuration, according to an embodiment.
Figure 34:
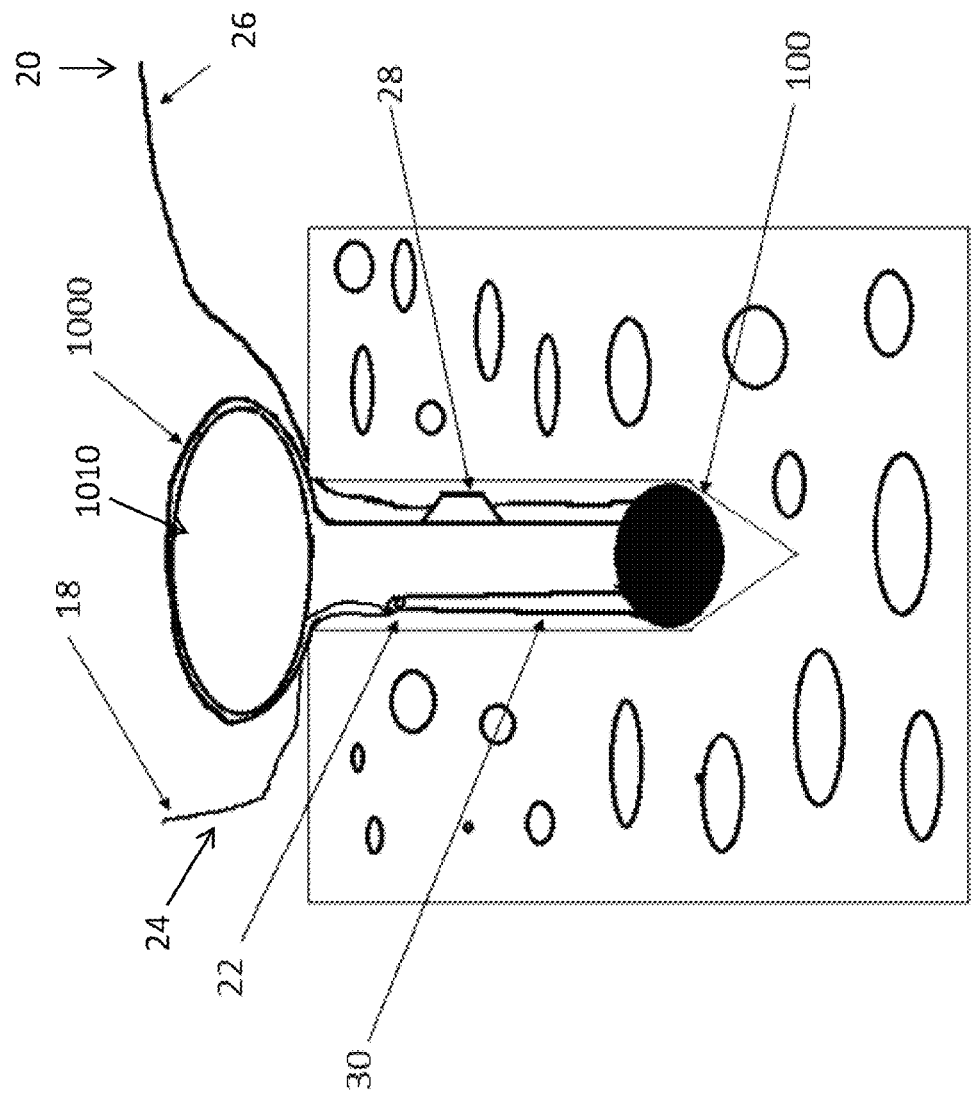
FIG. 34 is a side view schematic representation of the knotless instability anchor in the post-deployment configuration, according to an embodiment.
Figure 35:
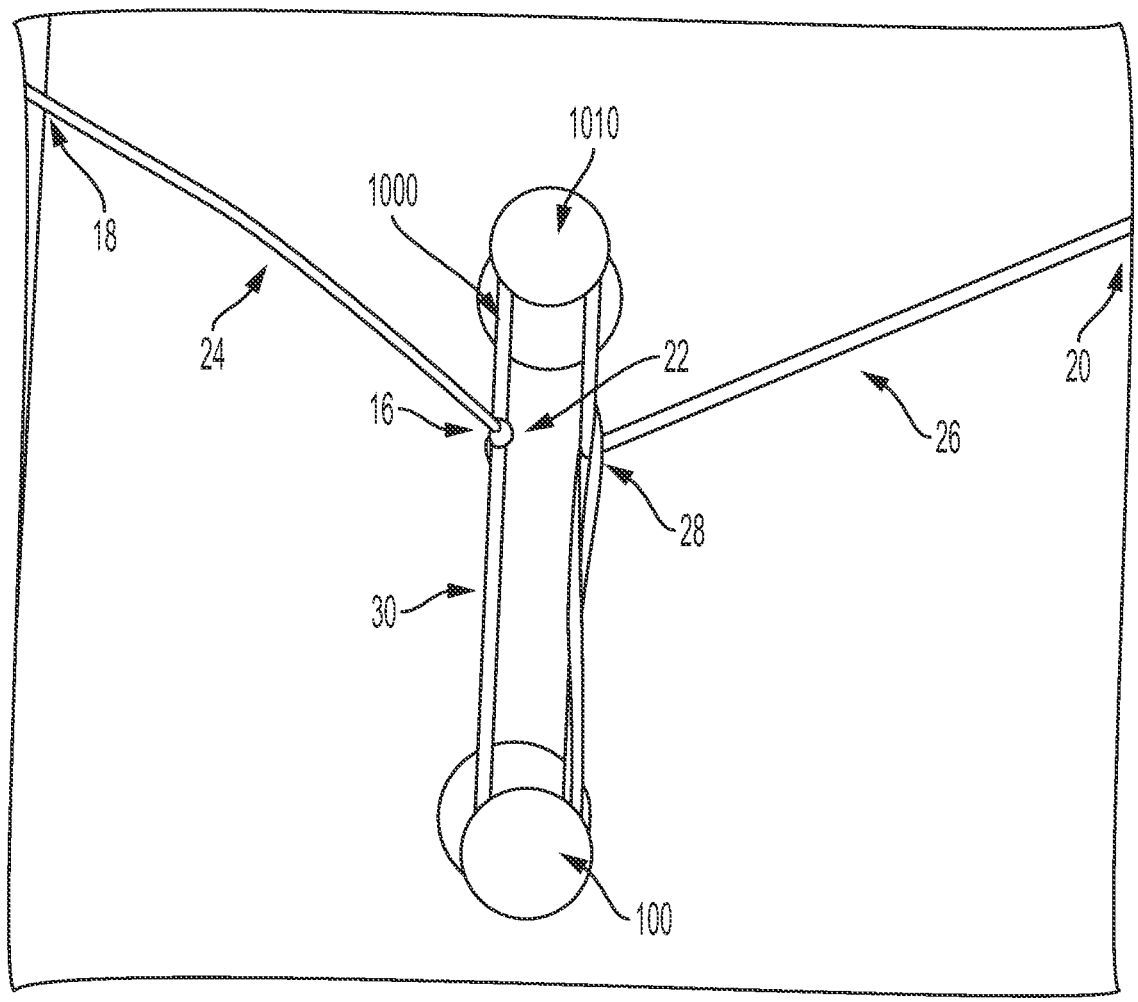
FIG. 35 is a side view schematic representation of the knotless instability anchor in the post-deployment configuration, according to an embodiment.

Still referring to FIG. 34, for placement of a detached tissue 1010 in a desired position relative to the bone, the passing limb 14 and the first limb 24 are positioned around or on opposing sides of the detached tissue 1010, as shown. Next, as shown in FIG. 8, the first limb 24 is passed through the adjustable loop 30 over the detached tissue 1010 (FIGS. 34-35). At the next step, the first limb 24 is pulled through the self-collapsing loop 22, as also shown in FIG. 8. To adjust the positioning of the tissue 1010 (FIG. 34) relative to the woven material 100, the second limb 26 is pulled. Pulling the second limb 26 in a direction away from the woven material 100 reduces the perimeter of the adjustable loop 30 and brings the tissue 1010 and the woven material 100 (and bone) closer together. When the tissue 1010 is in the desired location relative to the woven material 100 (and bone), the first limb 24 is pulled to collapse the self-collapsing loop 22, securing the tissue 1010 in relative position to the woven material 100 (and bone) (as should be understood by a person of ordinary skill in the art in conjunction with a review of this disclosure).

Pulling the first limb 24 and collapsing the self-collapsing loop 22 also causes a segment 1000 (FIG. 8) in the first limb 24 between the splice 28 and the aperture 16 to elongate. The segment 1000 elongates by virtue of the self-collapsing loop 22 getting smaller (in perimeter). As the self-collapsing loop 22 gets smaller and the segment 1000 elongates, the self-collapsing loop 22 rotates around the tissue 1010 to an opposing side of the woven material 100 in the bone hole, as shown in FIG. 34. As depicted in both FIG. 34 and FIG. 35, the self-collapsing loop 22 moves to position adjacent the adjustable loop 30, while the segment 1000 extends over and around the tissue 1010. In the post-deployment configuration, as shown in FIGS. 34 and 35, the first limb 24 and the second limb 26 extend from opposing sides of the knotless instability anchor 10, the woven material 100, and the tissue 1010. Finally, the first end 18 and the second end 20 of the suture stand 12 can be trimmed.

Turning now to FIGS. 9-30, there are shown various views schematic representations of a woven material (or soft anchor) 100, according to a multitude of embodiments, which can be used in conjunction with the knotless instability anchor 10 described herein. Generally, the following described and illustrated alternative all-suture anchor designs are configured to work with and be deployed by the driver 40 described herein in the same manner as the woven material 100 and other all-suture anchors, described and illustrated herein. The alternative embodiments of the woven material 100 can include a fibrous construct anchor body portion (or fibrous, braided or woven fabric-type structure such as a flexible web) and a suture or filament portion having a first end and a second end. The suture can pass through the anchor body in a number of ways (including woven, pass through a column, pierced through top and bottom, etc., as should be understood by a person of ordinary skill in the art in conjunction with a review of this disclosure). The anchor body can include a first state in which the anchor body is uncompressed and extends along the longitudinal axis of the suture when in an unfolded and pre-deployed condition; and a second state in which the flat anchor body is compressed and expanded in a direction perpendicular to longitudinal axis of the suture in a deployed condition (as discussed herein).

Figure 9:
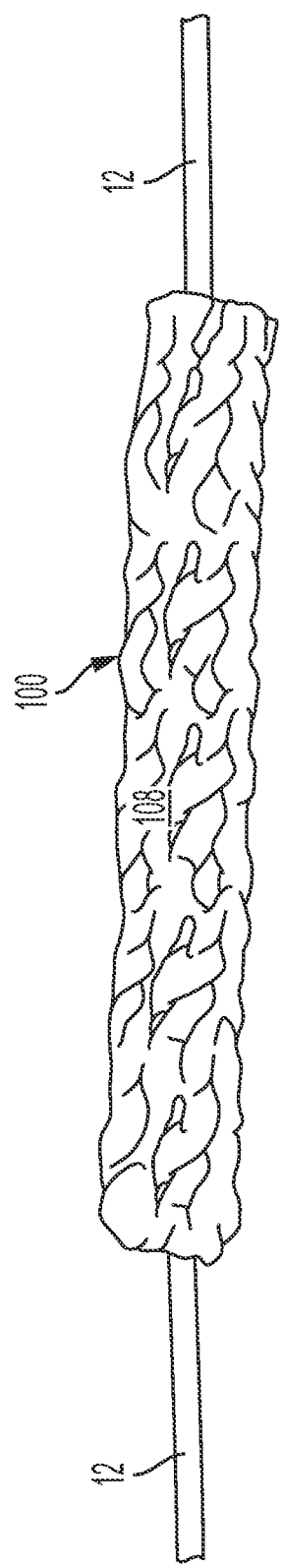
FIG. 9 is a back view schematic representation of a woven material, according to an alternative embodiment.
Figure 10:
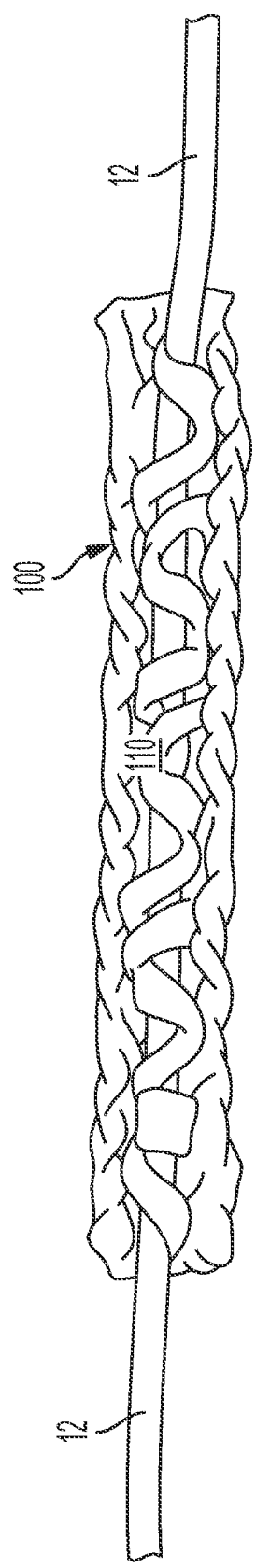
FIG. 10 is a top view schematic representation of the woven material of FIG. 9.
Figure 11:
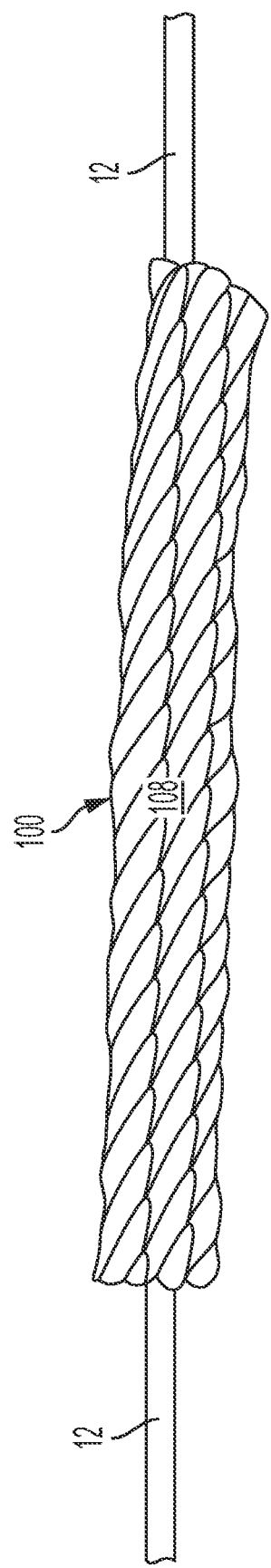
FIG. 11 is a back view schematic representation of a woven material, according to an alternative embodiment.
Figure 12:
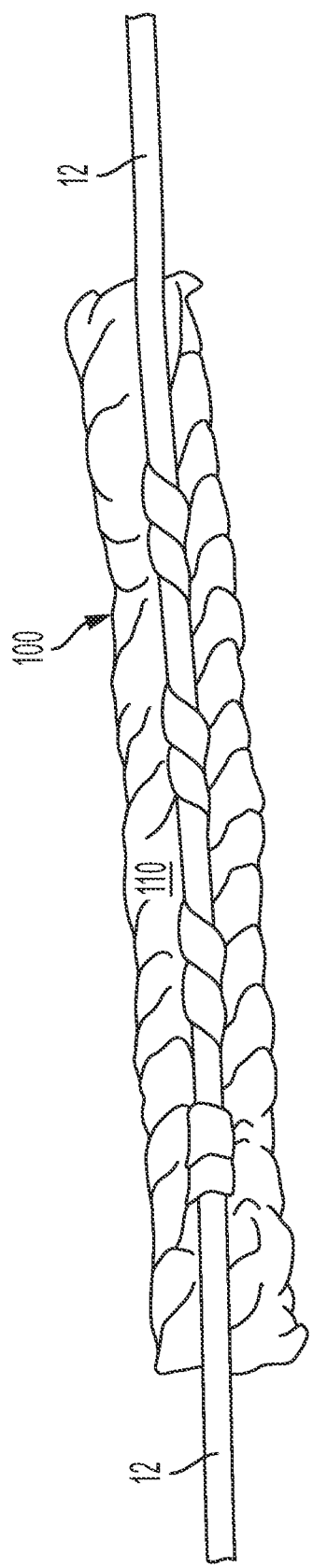
FIG. 12 is a top view schematic representation of the woven material of FIG. 11.

Referring briefly to FIGS. 9-12, there are shown front and back views schematic representations of a woven material 100, according to an embodiment. In FIGS. 9-12, the woven material 100 is an all-suture anchor braid. FIG. 9 shows a back view of an all-suture anchor 100, while FIG. 10 shows the front view. As shown, the length of suture 12 passing into and out of the woven material (i.e., anchor braid/fibrous construct) 100 only passes through one (e.g., "front") surface 110 of the anchor braid 100 (FIG. 10). Similarly, FIGS. 11-12 also show a back view (FIG. 12) and front view (FIG. 11) where the suture 102 passing only through one (e.g., "front") surface 110 of the anchor braid 100 (FIG. 12). When the all-suture anchor 100 has suture 12 passing only through one (e.g., "front") surface 110, the anchor braid 100 protects the suture 12 from abrasion on the opposing (e.g., "back") surface 108 (FIGS. 9 and 11) when loaded onto the driver 40 (as should be understood by a person of ordinary skill in the art in conjunction with a review of this disclosure). In FIGS. 9-12, the suture 12 is passed through the anchor braid 100 at numerous passing locations. In an embodiment, the number of passing locations is eight passing locations, while the number of passing locations for some alternative all-suture anchors 100 is six passing locations. The number of passing locations can vary depending on the composition and size of the suture 12 and/or anchor braid 100. The number of passing locations can be optimized by balancing input parameters, such as anchor braid length, anchor braid width, anchor braid pick density, suture diameter, and others, to yield output parameters, such as manufacturability, anchor creep under load, and pullout strength.

Figure 13:
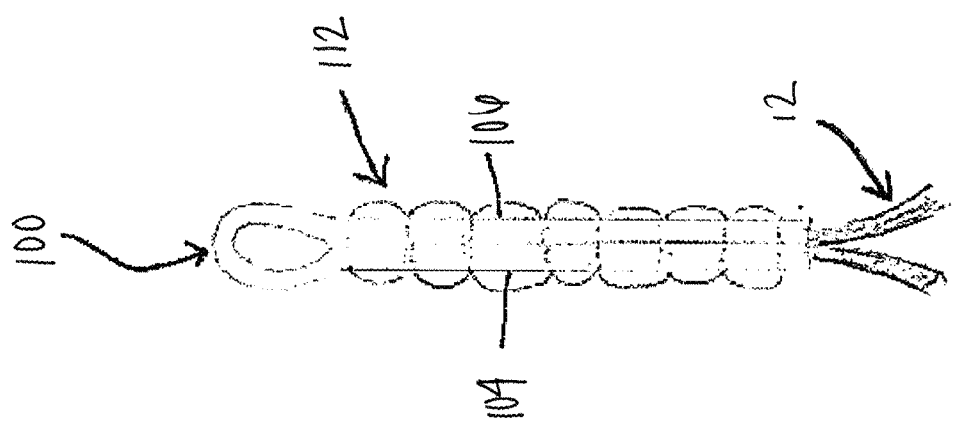
FIG. 13 is a top view schematic representation of a woven material folded and stitched, according to an embodiment.
Figure 14:
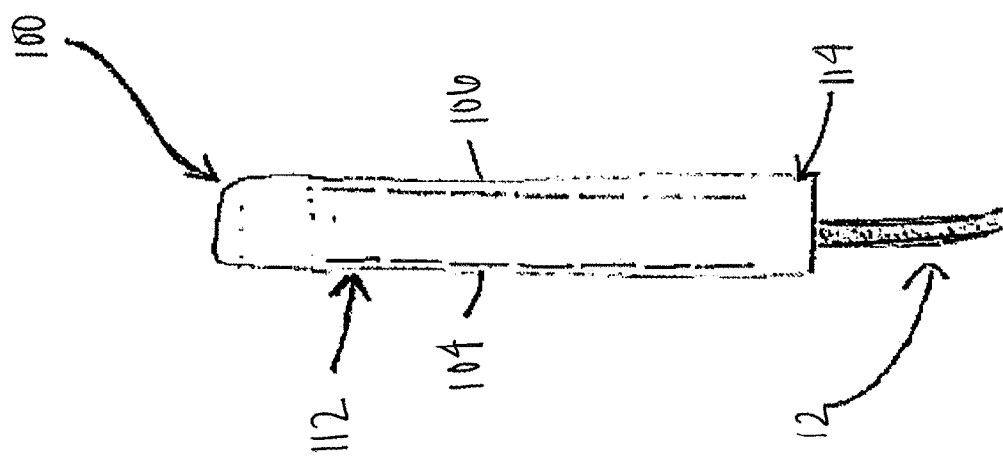
FIG. 14 a top view schematic representation of a woven material of FIG. 13 with an additional material covering.

Turning now to FIGS. 13-14, there are shown top views schematic representations of an alternative embodiment of a woven material 100. In FIGS. 13-14 the woven material 100 is an anchor braid 100 with an additional material 112. One of ordinary skill in the art should recognize and appreciate potential embodiments of a Y-Knot anchor with additional material, such as monofilament polymers, to add strength. Additional material 112 can be applied to the all-suture anchor 100. As shown in FIG. 13, the anchor braid 100 is folded in half. A monofilament 112 is used to stitch together each (i.e., two) side edge 104, 106 of the anchor braid 100 to create an enclosed area 114 with the length of suture 12 inside, as shown in FIG. 14. In addition to improved strength, this will prevent the anchor braid 100 from rolling over on itself during insertion and exposing the suture 12 to the bone, causing abrasion. Additionally, the described twisting of the anchor braid 100, in combination with a more dense material running in the axis of the anchor braid 100 can result in a threaded all-suture anchor 100.

Figure 15:
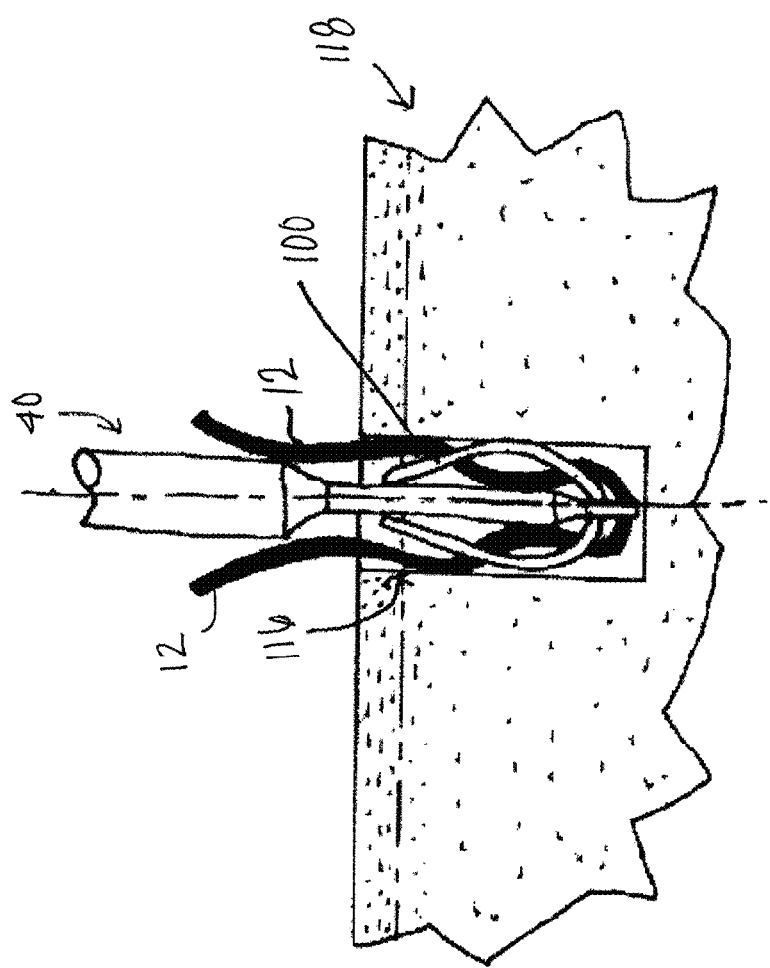
FIG. 15 is a side view schematic representation of an embodiment of a woven material in the undeployed state, according to an alternative embodiment.
Figure 16:
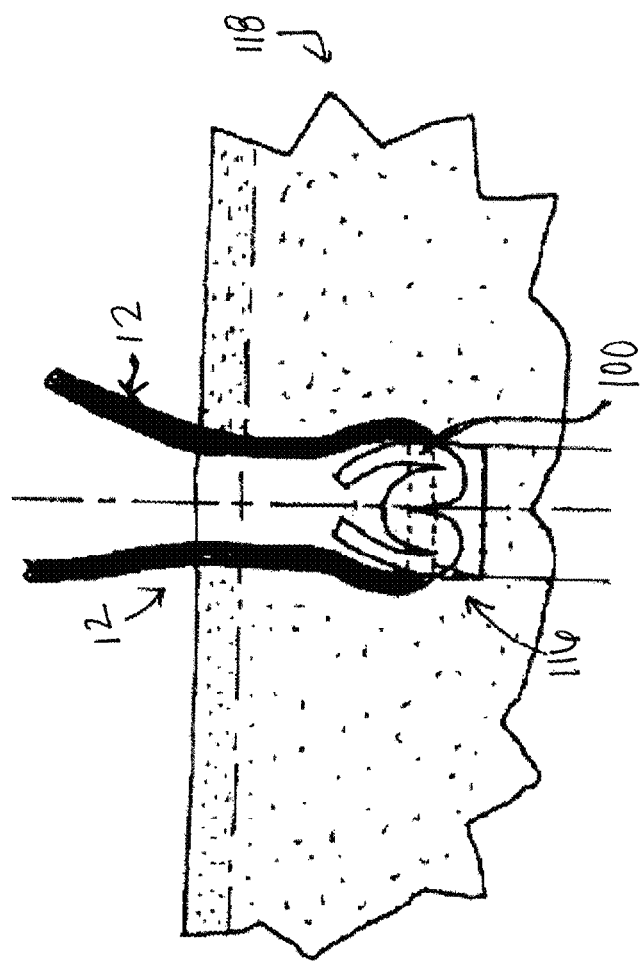
FIG. 16 is a side view schematic representation of the woven material of FIG. 15 shortened and expanded in the deployed state, according to an alternative embodiment.

Turning now to FIGS. 15-16, there are shown side view schematic representations of an embodiment of an alternative embodiment of a woven material 100 in the pre-deployment and post-deployment configurations. In the depicted embodiment, the woven material 100 is a soft all-suture anchor, such as the Y-Knot® anchor. One such suture anchor is disclosed in U.S. Pat. No. 9,826,971 assigned to the assignee hereof and incorporated by reference herein in its entirety.

An embodiment of the Y-Knot® anchor (or soft anchor or "all-suture" anchor) 100 is illustrated in detail in FIGS. 15-16. The Y-Knot® anchor 100, as shown in FIGS. 15-16, contains at least two sections: at least one suture 12, which is a suture to be anchored; and an anchor body 100 (e.g., fibrous construct, as should be understood by those of ordinary skill in the art in conjunction with a review of this disclosure), which is to form a portion of the anchor 100 that can increase in width, thickness and/or diameter and shrink in length as part of deployment. See FIG. 15, showing the anchor body 100 in the pre-deployment configuration; and FIG. 16, showing the anchor body 100 "shortened" and "expanded" in the post-deployment configuration, which is additive to the increase due to the pleats. This soft anchor embodiment also takes advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body 100 that increases in width, thickness and/or diameter at deployment, it should be understood that the suture 12 can also play a role in the deployment of the anchor 100 even though the suture 12 may remain free (in some embodiments) to slide, and non-slidable in others (at least at a particular position or point in use) in relation to the anchor body 100. The suture 12 helps to position, align and support the anchor body 100, such that if the suture 12 were to be removed from the anchor body 100 after deployment of the anchor 100, the anchor body 100 may be free to spill (i.e., release), allowing the anchor body 100 to collapse and shrink in size, allowing for easy (and potentially undesirable) removal.

In other words, the anchor body 100 has two primary functions. First, it becomes a base for the suture 12 to slide within. Second, when compressed and/or pleated during deployment, the anchor body 100 becomes more compact in one direction thereby expanding outwardly and increasing its overall width, thickness or diameter to create a retention capacity. This action of having the anchor body 100 change in shape to increase its overall width, thickness or diameter is a useful characteristic which may be used advantageously to secure the anchor 100 in a hole 116 or against a bony or soft tissue 118. It is this combination of the expanding anchor body 100 coupled with the suture 12 remaining slidable (in some embodiments; and non-slidable in others, at least at a particular position or point in use) in relation to the anchor body 100 that render embodiments of the present invention ideal for the reattachment of soft tissue to bone 118 or soft tissue to soft tissue where it is desirable to pass sliding knots to secure a repair.

Figure 17:
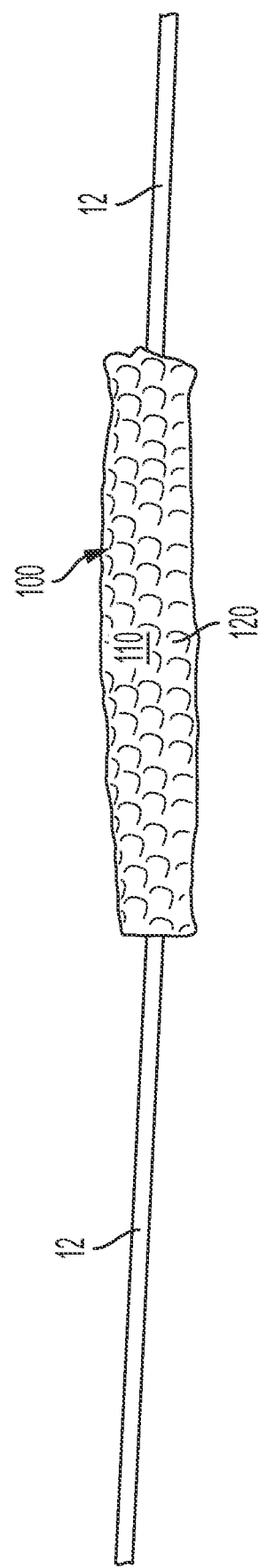
FIG. 17 is a top view schematic representation of an woven material, according to an alternative embodiment.
Figure 18:
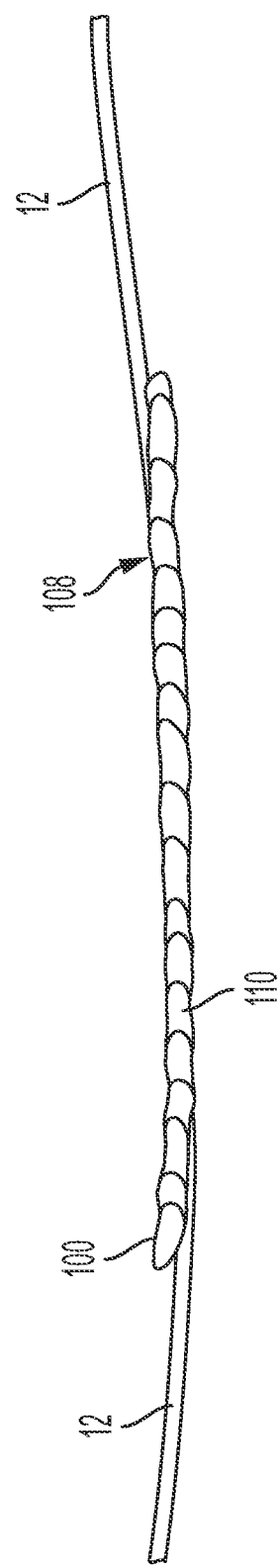
FIG. 18 is a side view schematic representation of the woven material in FIG. 17.

Turning briefly to FIGS. 17-18, there are shown top and side views schematic representations of a woven material 100, according to an alternative embodiment. In FIGS. 17-18 the woven material 100 is an all-suture anchor braid. As shown in FIGS. 17-18, the length of suture 12 passes through an approximate center 120 of the anchor braid 100. In the depicted embodiment, the length of suture 12 enters the anchor braid 100 through one (e.g., "front") surface 110 and exits through the opposing (e.g., "back") surface 108 of the anchor braid 100. With the length of suture 12 positioned on both sides of the anchor braid 100, the anchor braid 100 can be loaded onto the driver 40 such that anchor braid 100 can be positioned against a bone, while the lengths of suture 12 are along the driver 40.

Figure 19:
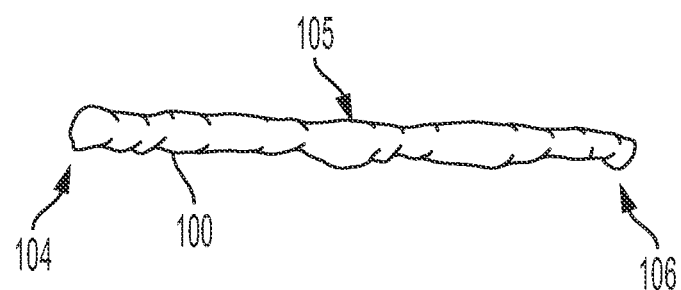
FIG. 19 is a top view schematic representation of a woven material with a central eyelet, according to an alternative embodiment.
Figure 20:
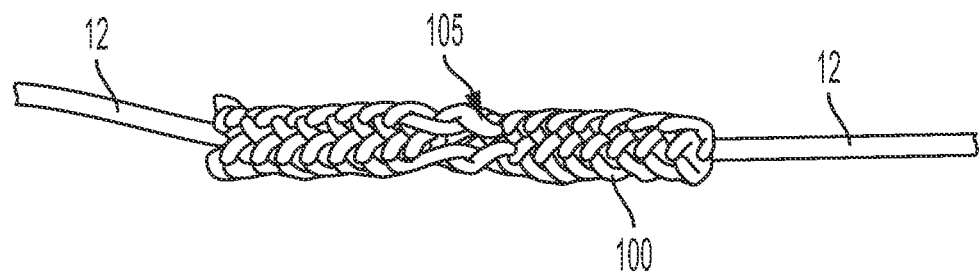
FIG. 20 is a top view schematic representation of the woven material of FIG. 19 with a length of suture passing through the central eyelet.

Referring now to FIGS. 19-20, there are shown top views schematic representations of a woven material 100, according an additional alternative embodiment. In FIGS. 19-20, the woven material 100 is an all-suture inverted anchor braid 100. To create an inverted anchor braid 100, a threader with a threader loop is first passed through the anchor braid 100. Then, in an end of the anchor braid 100 is pulled through the threader loop. Finally, the threader loop is pulled back through the anchor braid 100, creating a central eyelet 105, as shown in FIG. 19. A length of suture 12 can be loaded onto the inverted anchor braid 100 by passing the length of suture 12 through the anchor braid 100, as described in conjunction with any of the embodiments herein, and passing through the central eyelet 105, as shown in FIG. 20.

Figure 21:
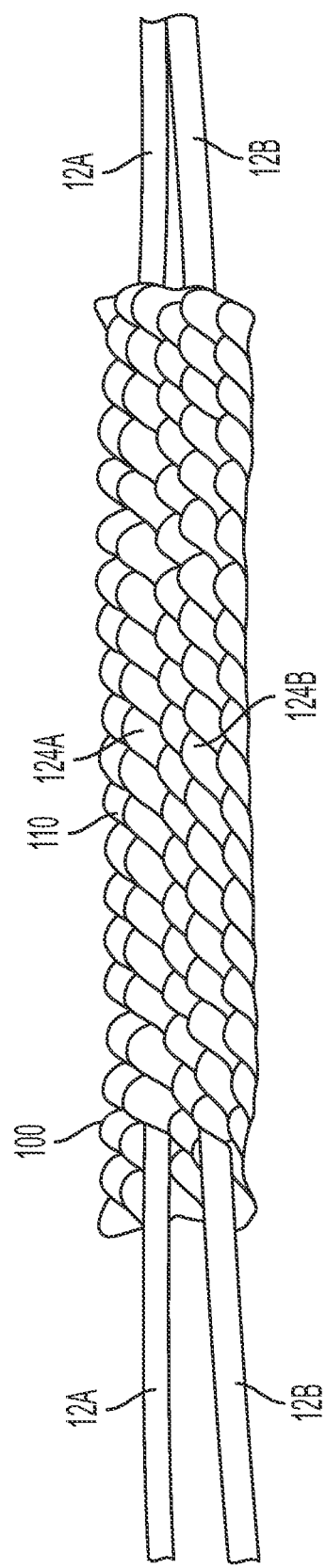
FIG. 21 is a top view schematic representation of a woven material loaded with two lengths of suture, according to an alternative embodiment.
Figure 22:
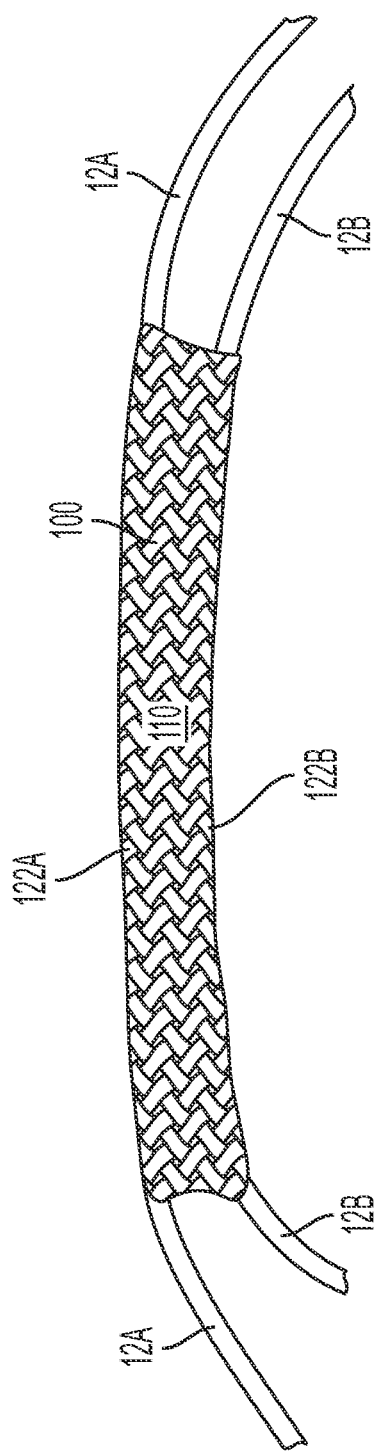
FIG. 22 is a top view schematic representation of a woven material loaded with two lengths of suture, according to an alternative embodiment.

In another alternative embodiment, as shown in FIGS. 21-22, the woven material 100 is an anchor braid 100 loaded with multiple lengths of suture 12A, 12B. In the depicted embodiment, the anchor braid 100 is loaded with two lengths of suture 12A, 12B. The lengths of suture 12A, 12B may extend through the anchor braid 100 along its opposing edges 122A, 122B (FIG. 22), through two off-center locations 124A, 124B (FIG. 21), or any conceivable combination thereof (including an extension of the length of suture 12A, 12B through the approximate center 120 of the anchor braid 100). In addition, the lengths of suture 12A, 12B may enter/exit the anchor braid 100 on the same surface (FIGS. 9-12) or on opposing surfaces (FIGS. 17-18).

Figure 23:
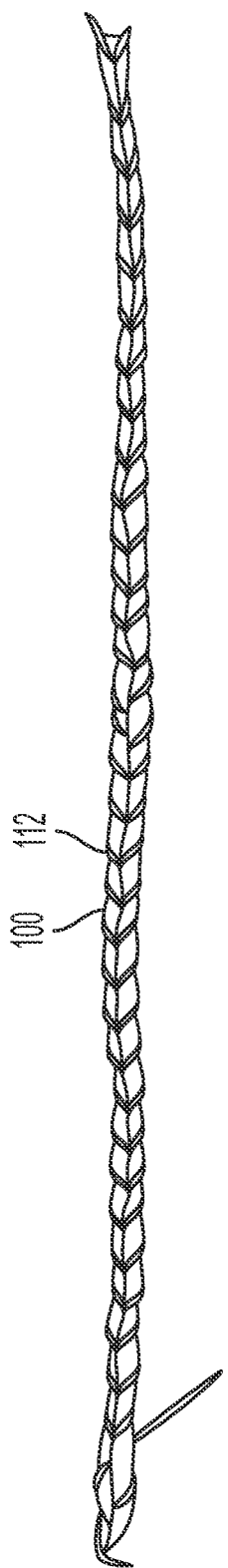
FIG. 23 is a top view schematic representation of a woven material with an additional monofilament, according to an alternative embodiment.
Figure 24:
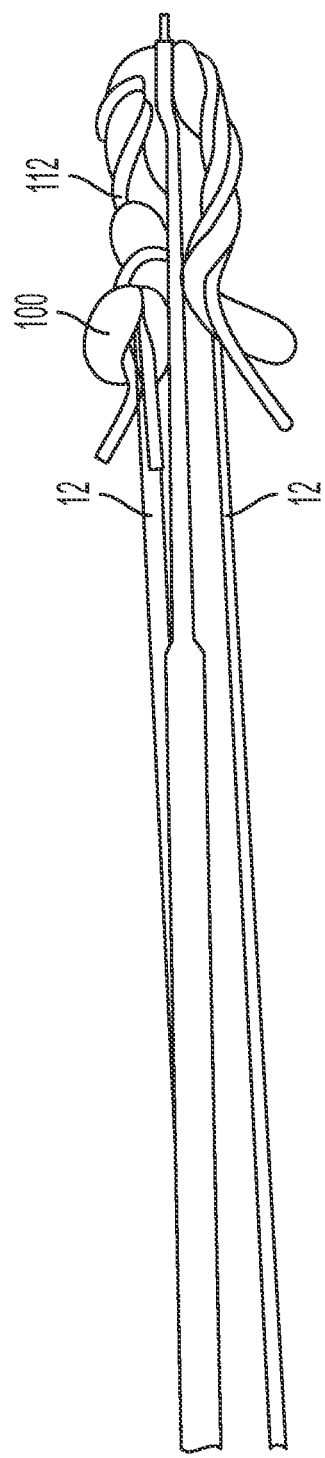
FIG. 24 is a side view schematic representation of the woven material of FIG. 23 loaded on an inserter (or driver)

In yet another alternative embodiment, as shown in FIGS. 23-24, the woven material 100 is an all-suture anchor comprised of flat braid, tube braid, cored suture, segmented suture of multiple densities, or suture with a contrasting density. The anchor 100 in FIGS. 23-24 includes an additional braided monofilament 112, for example. The additional braided monofilament 112 is woven around and through the anchor, as shown in FIG. 23. The additional braided monofilament 112 provides an additional form of fixation by creating irregularity within the bone surface via the added monofilament braid 112, additional anchor "locking" between the multi suture densities (interdigitation of monofilament co-mingled with UHMWPE braid locking/flipping) and/or the creation of rigid mechanical "barbs" on the exterior surface of the anchor 100 that are deployed via the base density of a UHMWPE braid. Lengths of suture (not shown) may enter/exit the anchor 100 as described above.

In accordance with another embodiment, the woven material 100 has an open elongated column/lumen extending from a first end to a second end; and the suture 12 passes through and is positioned at least partially in the open column. In an embodiment, the suture 12 is free to slide through the open column such that the suture 12 can be removed from the open column from the first end of the woven material 100 and the second end of the woven material 100. An embodiment of the woven material 100 can also be tubular in addition to having an open elongated column/lumen. The suture 12 may either be woven in situ directly onto the flat tape/woven material 100 (e.g., a round section suture braid), or woven with an open column into which the round section suture braid may be later inserted.

Figure 25:
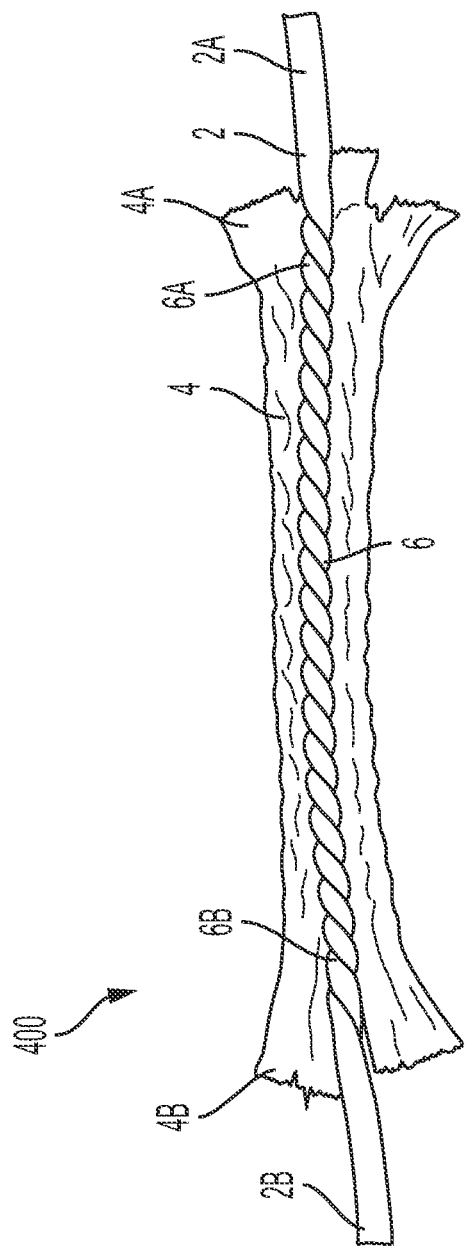
FIG. 25 is a perspective view digital photograph of a woven material in an unloaded (not loaded onto an installation device or inserter), pre-deployment configuration according to an alternative embodiment.

In particular, as seen in FIG. 25, a perspective view schematic representation of a woven material 400 in an unloaded (not loaded onto an installation device or inserter), pre-deployment configuration, according to an embodiment. In the depicted embodiment, the woven material 400 is a soft all-suture anchor. The all-suture anchor 400 can include, but is not limited to, a flat fibrous construct 4 having a first end 4A, a second end 4B, and an open elongated column/lumen 6 having a first end 6A and the second end 6B (each of the first end 6A and the second end 6B of the open elongated column/lumen 6 can extend between or beyond the first 4A and second 4B ends of the flat fibrous construct). The open elongated column/lumen 6 can be woven along an axis that is parallel to or along a central axis of the flat fibrous construct 4, or can be woven along a path that is not parallel to the central axis. As shown in FIG. 25, the open elongated column/lumen is woven along the central axis.

Still referring to FIG. 25, a filament 2 is shown having a first end 2A and a second end 2B, and passing through and at least partially positioned in the open column 6. In an embodiment, the filament 2 is free to slide through the open column 6 such that the filament 2 can be removed from the open column 6 from the first end 2A of the fibrous construct 2 and/or the second end 2B of the fibrous construct 2. In accordance with an alternative embodiment, the filament is locked and not slidable through the open column 6.

Figure 26:
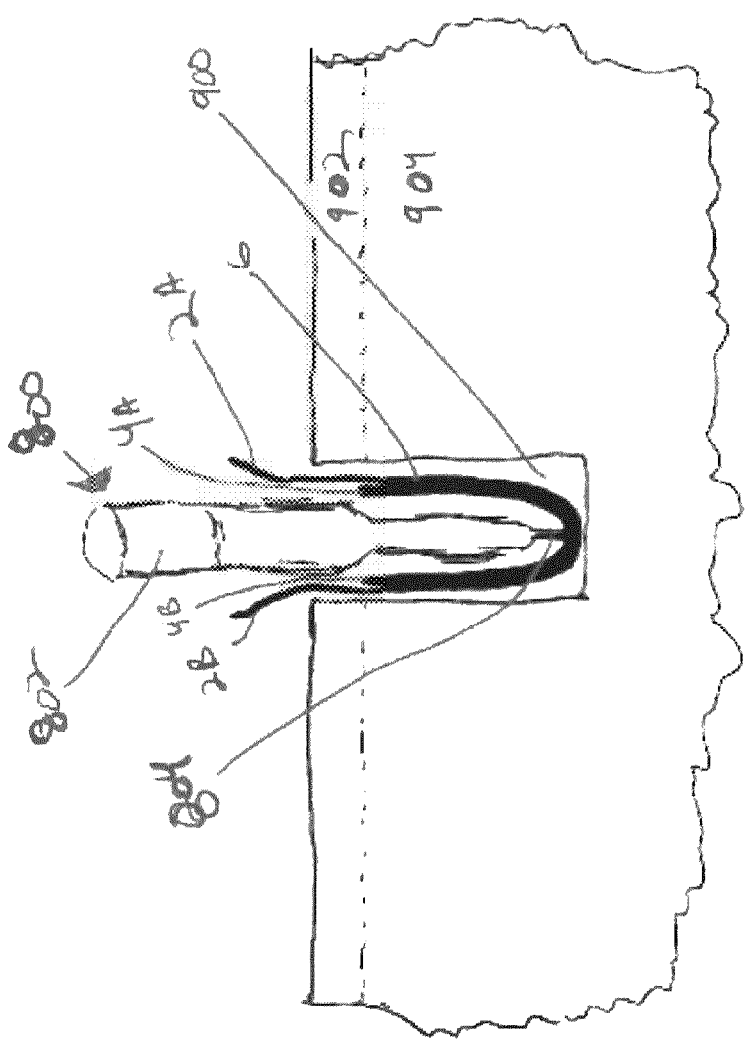
FIG. 26 is a side view schematic representation of an embodiment of the woven material of FIG. 25 connected to an installation device or inserter in a pre-deployment configuration.
Figure 27:
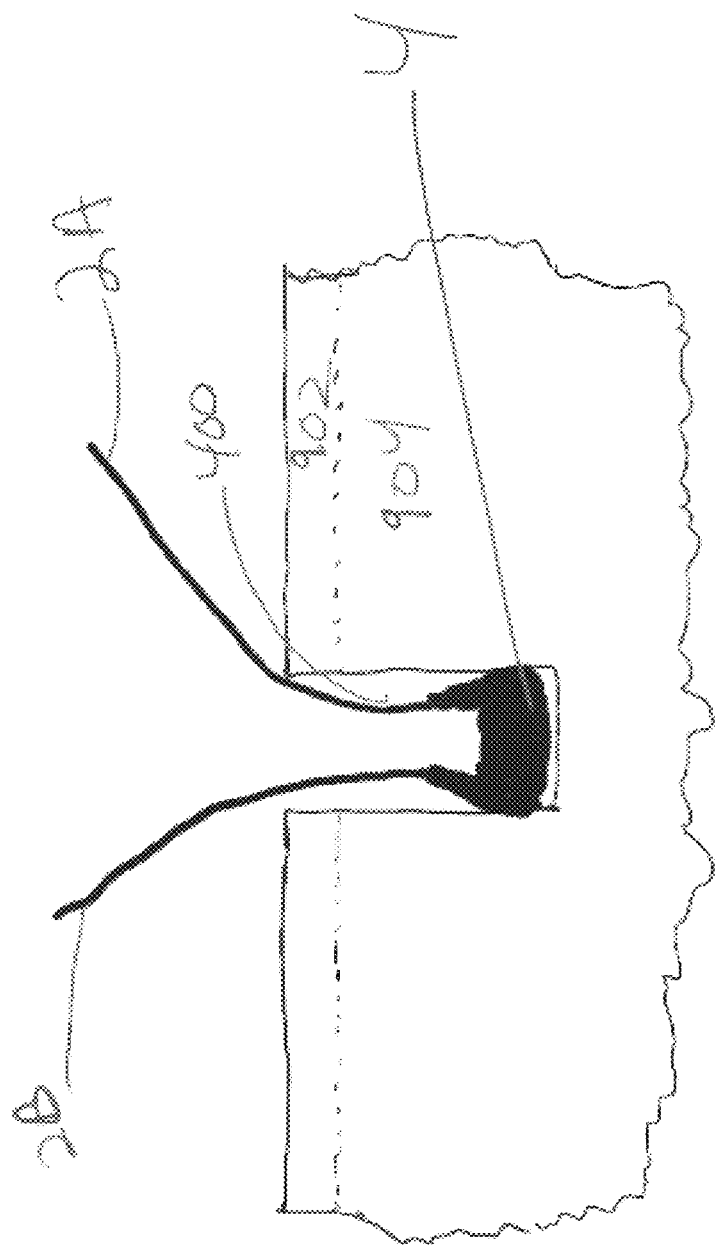
FIG. 27 is a side view schematic representation of an embodiment of the woven material of FIG. 25 in a post-deployment configuration positioned in a bone hole.
Figure 28:
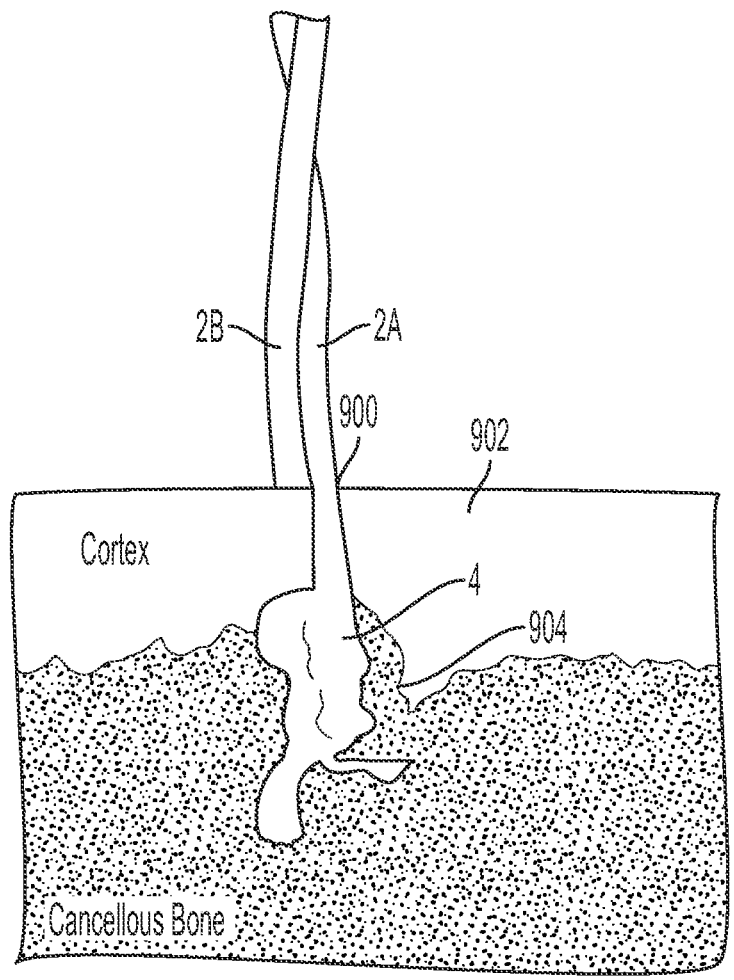
FIG. 28 is a side view digital photograph of an embodiment of the woven material of FIG. 25 in a post-deployment configuration positioned in a bone hole.

Turning now to FIGS. 26 and 27, there are shown side view schematic representations of an embodiment of the all-suture anchor 400 in the pre-deployment and post-deployment configurations. As described above, the all-suture anchor 400 contains at least two sections: at least one suture 2 with a first end 2A and a second end 2B; and an anchor body/fibrous construct 4 with a first end 4A and a second end 4B, and an open elongated column/lumen 6 extending from a first end 6A to a second end 6B, which is to form a portion of the anchor 400 that can increase in width, thickness and/or diameter and shrink in length as part of deployment.

As shown in FIG. 26, the installation device (or driver 40, as described herein above) in the pre-deployment configuration is provided. The all-suture anchor 400 is shown connected to the distal deployment end 804 of an installation device 800 (which can be a driver 40 of an embodiment described herein), which also includes a handle 802. The distal deployment end 804 and the all-suture anchor 100 are shown positioned in a bone hole 900 in cancellous bone 904 under the bone cortex 902. In order to deploy the all-suture anchor 400 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 900 with or without the installation device 800 in place in the bone hole 900 (if installation device 800 is in place in the bone hole 900, it can act as a counter force to the tension force out of the hole 900 to assist with the deployment of the all-suture anchor 400).

As shown in FIG. 27, the anchor body/fibrous construct 4 is shown "shortened" and "expanded" in the post-deployment configuration and locked in the bone hole 900, which can be additive to the increase due to pleats formed by the fibrous construct 4 (which may also be part of the fibrous construct 4). See also FIG. 28. The all-suture anchor 400, and, in particular, the fibrous construct 4 takes advantage of Poisson's ratio (as described with respect to other anchors, above), which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 400 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 400 in a hole 900 or against a bony or soft tissue. It is this combination of the expanding anchor body 4 coupled with the suture 2 remaining slidable (in some embodiments; and non-slidable in others, at least at a particular position or point in use) in relation to the anchor body 4 that render embodiments of the present invention ideal for the reattachment of soft tissue to bone or soft tissue to soft tissue where it is desirable to pass sliding knots to secure a repair.

In one embodiment, an inventive configuration, structure, and resulting function of a soft all-suture anchor that utilizes a hybrid combination of soft implantable materials is provided. A hybrid soft all-suture anchor of an embodiment includes superior pull-out strength properties as compared to conventional soft all suture anchors. Embodiments of the present invention provide a better soft all-suture anchor for use in hard bone, due in part to a hybrid expanding component portion. These embodiments are also suitable for use in soft cancellous bone where there is a very thin or weak cortical layer. The hybrid all-suture anchor can include, but is not limited to, an expandable member/portion configured to increase in size from a first pre-deployed condition to a second deployed condition upon the application of an activator; and a filament having a first filament end and a second filament end, and positioned in contacting relation to the expandable member in the second deployed condition. The anchor can also include a flat fibrous construct having a first end and a second end, and wherein the filament passes through the fibrous construct. The flat fibrous construct includes a first state in which the flat fibrous construct is uncompressed and extends along the longitudinal axis of the filament when in an unfolded and pre-deployed condition; and a second state in which the flat fibrous construct is compressed and expanded in a direction perpendicular to longitudinal axis of the filament in a deployed condition. The structure, configuration, and functionality of the expandable member, and of the fibrous construct (when part of an embodiment), help to set and hold the anchor in the bone hole in a post-deployment condition. The expandable portion/member can be part of a hybrid all-suture anchor used with any filament portion (as described herein) only. The expandable portion/member can also be part of a hybrid all-suture anchor used with any filament portion and any fibrous construct portion (as described herein).

Figure 29:
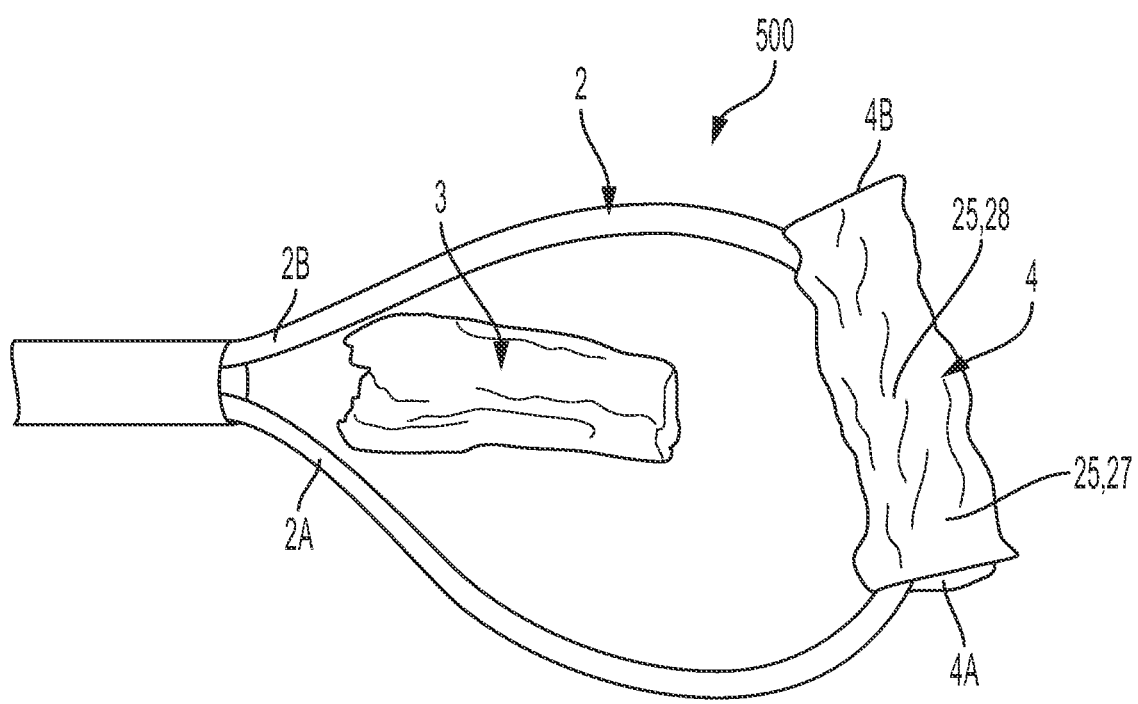
FIG. 29 is a perspective view digital photograph of a woven material in an unloaded (not loaded onto an installation device or inserter), pre-deployment configuration according to an alternative embodiment.

For example, referring to FIG. 29, a perspective view of a hybrid soft all-suture anchor 500 in a pre-deployment configuration, according to an embodiment is shown. The hybrid all-suture anchor 500 can include, but is not limited to, a flat fibrous construct 4 having a first end 4A, a second end 4B. A filament 2 is shown having a first end 2A and a second end 2B, and woven, threaded, or otherwise passing through the fibrous construct 4 at passing locations 25, 27 and 25, 28. See U.S. Pat. No. 9,826,971 for a further description of the structural aspects of the filament and fibrous construct, which is part of this example of the invention (as should be understood by a person of ordinary skill in the art in conjunction with a review of this disclosure).

In an embodiment, the filament 2 is free to slide through the fibrous construct 4 (and the expandable portion 3 when attached thereto) such that the filament 2 can be removed from the fibrous construct 4 from the first end 4A of the fibrous construct 4 and/or the second end 4B of the fibrous construct 4. In accordance with an alternative embodiment, the filament is locked and not slidable through the fibrous construct 4 and/or the expandable portion 3 (when attached to the expandable portion 3).

Figure 30:
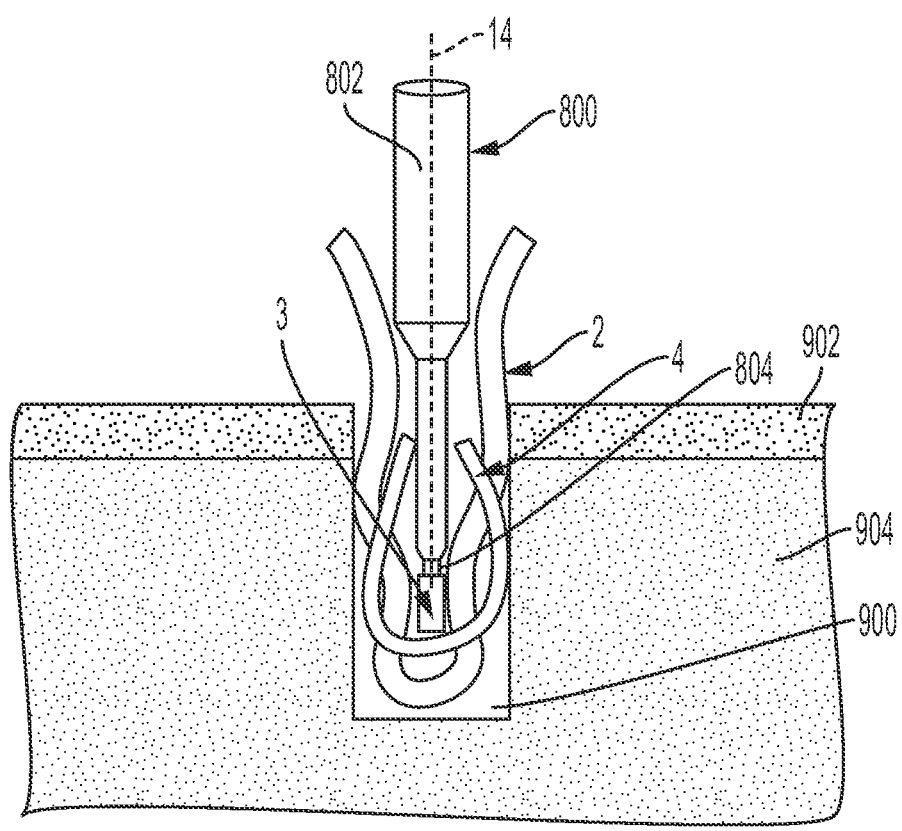
FIG. 30 is a side view schematic representation of an embodiment of the woven material of FIG. 29 connected to an installation device or driver in a pre-deployment configuration.
Figure 31:
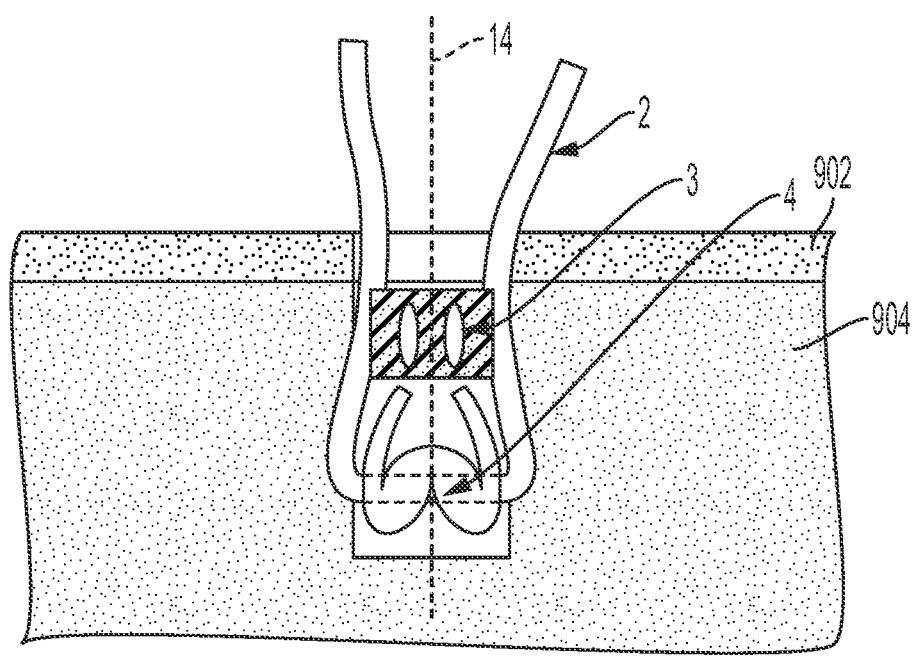
FIG. 31 is a side view schematic representation of an embodiment of the woven material of FIG. 29 in a post-deployment configuration positioned in a bone hole.

Turning now to FIGS. 30 and 31, there are shown side view schematic representations of an embodiment of the all-suture anchor 500 in the pre-deployment and post-deployment configurations. As described above, the all-suture anchor 500 contains at least two sections: at least one suture 2 with a first end 2A and a second end 2B; and an anchor body/fibrous construct 4 with a first end 4A and a second end 4B, which is configured to form a portion of the anchor 500 that can increase in width, thickness and/or diameter and shrink in length as part of deployment. The all-suture anchor 500 also includes an expandable portion 3 which is configured to form a portion of the anchor 500 that can increase in size in the post-deployment configuration in response to an activator (as should be understood by a person of ordinary skill in the art in conjunction with a review of this disclosure).

As shown in FIG. 30, the installation device (or inserter, as described herein above) in the pre-deployment configuration is provided. The all-suture anchor 500 is shown connected to the distal deployment end 804 of an installation device 800 (which can be an inserter, as described herein above), which also includes a handle 802. The distal deployment end 804 and the all-suture anchor 500 are shown positioned in a bone hole 900 in cancellous bone 904 under the bone cortex 902. In order to deploy the all-suture anchor 500 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 900 with or without the installation device 800 in place in the bone hole 900 (if installation device 800 is in place in the bone hole 900, it can act as a counter force to the tension force out of the hole 900 to assist with the deployment of the all-suture anchor 500). In addition, an activator can be added to the anchor to cause the expandable portion to expand to a second size greater than the first pre-deployment size. In one embodiment, the activator is water.

As shown in FIG. 31, the anchor body/fibrous construct 4 is shown "shortened" and "expanded" in the post-deployment configuration and locked in the bone hole 900, which can be additive to the increase due to pleats formed by the fibrous construct 4 (which may also be part of the fibrous construct 4). The all-suture anchor 500, and, in particular, the fibrous construct 4 takes advantage of Poisson's ratio (similarly, as discussed above), which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 500 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 500 in a hole 900 or against a bony or soft tissue. It is this combination of the expanding anchor body 4 coupled with the suture 2 remaining slidable (in some embodiments; and non-slidable in others, at least at a particular position or point in use) in relation to the anchor body 804 that render embodiments of the present invention ideal for the reattachment of soft tissue to bone or soft tissue to soft tissue where it is desirable to pass sliding knots to secure a repair.

Figure 32:
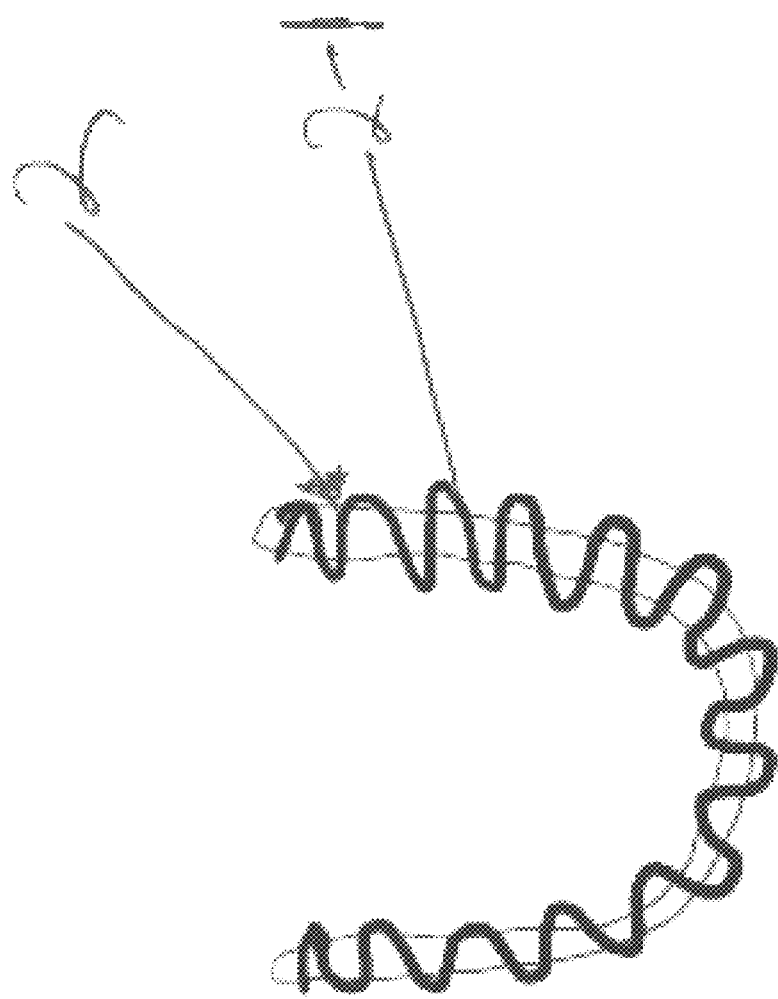
FIG. 32 is a side view schematic representation of a portion of a woven material according to an alternative embodiment.

Still referring to FIG. 31, the expandable portion 3 is shown in the expanded second size, greater than the first smaller pre-deployment size, after exposure to the activator. The expandable portion expands greatly in volume when exposed to the activator, causing it to wedge in the bone hole 900 and lock the anchor 500 in place. In accordance with an embodiment, in order to tension the filament 2 to reattach soft tissue (not shown), the filament 2 can freely slide backward and forward through the fibrous construct 4 and through the expandable portion 3 (as may be necessary when connected to the expandable portion 3). In certain situations without the presence of fibrous construct 4, the free sliding filament 2 could potentially cut through the expandable portion 3 resulting in a less than optimum deployment of the all-suture anchor 500. As such, in some embodiments of the all-suture anchor 500 with or without the fibrous construct 4, a second short length of suture 2-1 could be wrapped or looped around the filament 2 (see FIG. 32) to prevent sawing/cutting through the expandable portion 3 by the filament 2 when in contacting relation with the expandable portion 3.

Figure 33:
FIG. 33 is a side view digital photograph of an embodiment of the woven material of FIG. 29 in a post-deployment configuration after addition of an activator.

Turning to FIG. 33, a side view digital photograph of an embodiment of the all-suture anchor of FIG. 29 in a post-deployment configuration after addition of an activator according to an embodiment is shown. As shown, the expandable portion 3 has increased in size to a second deployed structural condition (bone hole is not shown to illustrate the extent of expansion of expandable portion 3), and the filament 2 is positioned through and/or in otherwise contacting relation with the expandable portion 3.

Similarly with respect to the filament 2 and fibrous construct 4 described above and the embodiments shown in FIGS. 30-32, the expandable portion 3 can be a part of any all-suture anchor described herein or otherwise including the all-suture anchor shown and described in U.S. Patent application Ser. No. 16/033,616. The same structure and functionality of the expandable portion 3 described above and shown in FIGS. 30-32 can apply to these embodiments of an all-suture anchor (with and without the fibrous construct).

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A knotless instability anchor, comprising:
   an anchor having a first side and a second side with a suture material passing therethrough from the first side to the second side,
   wherein the suture material has an adjustable loop extending from the first side of the anchor and a first limb and a second limb extending from the second side of the anchor;
   a splice formed in the first limb between a first end of the first limb and the anchor;
   a self-collapsing loop formed in the first limb between the first end and the splice;
   wherein the second limb extends through the splice in the first limb; and
   wherein the first limb is configured to be pulled to decrease the perimeter of the self-collapsing loop from a first size to a second size smaller than the first size.

2. The anchor of claim 1, wherein the self-collapsing loop is formed in the first limb by passing the second end of the second limb through an aperture in the first limb.

3. The anchor of claim 1, wherein the suture material is one continuous strand of suture.

4. The anchor of claim 1, wherein the suture material passes through the anchor at more than one passing location.

5. The anchor of claim 1, wherein the second limb is configured to be pulled to decrease a perimeter of the adjustable loop from a first size to a second size smaller than the first size.

6. The anchor of claim 1, wherein the anchor is selected from the group consisting of an all-suture anchor.

7. The anchor of claim 1, further comprising a passing limb releasably connected to the adjustable loop.

8. The anchor of claim 1, further comprising a segment between the splice and the self-collapsing loop in the first limb which increases in length when a perimeter of the self-collapsing loop decreases.

9. The anchor of claim 1, further comprising a driver with the knotless instability anchor loaded thereon.

10. The anchor of claim 1, wherein the first limb is configured to pass through the adjustable loop and the self-collapsing loop.

11. A method of securing a first body in relative position to a bone hole, the method comprising the steps of:
    providing a knotless instability anchor comprising an anchor having a first side and a second side with a suture material passing therethrough from the first side to the second side, wherein the suture material has an adjustable loop extending from the first side of the anchor and a first limb and a second limb extending from the second side of the anchor, a splice formed in the first limb between a first end of the first limb and the anchor, and a self-collapsing loop formed in the first limb between the first end and the splice;
    passing the second limb through the splice in the first limb;
    attaching a passing limb to the adjustable loop via a releasable connection;
    implanting the anchor into a bone hole;
    passing the first limb over at least a portion of the first body to an opposing side of the first body;
    pulling the first limb through the adjustable loop on the opposing side of the first body; and
    pulling the first limb to decrease the perimeter of the self-collapsing loop to a second size smaller than the first size.

12. The method of claim 11, further comprising the step of pulling the first limb through the self-collapsing loop on the first limb.

13. The method of claim 12, further comprising the step of pulling the second limb to decrease a perimeter of the adjustable loop to a second size smaller than the first size.

14. The method of claim 11, wherein decreasing the perimeter of the self-collapsing loop increases a length of a segment between the splice and the self-collapsing loop.

15. The method of claim 11, wherein decreasing the perimeter of the self-collapsing loop rotates the self-collapsing loop to the opposing side of the first body.

16. The method of claim 11, further comprising the step of loading the knotless instability anchor onto a driver.

17. The method of claim 11, wherein the first body is a tissue.

18. The method of claim 11, wherein the anchor is an all-suture anchor.

* * * * *